(12) United States Patent
Hartmann et al.

(10) Patent No.: US 6,559,157 B2
(45) Date of Patent: May 6, 2003

(54) DIHYDRONAPHTHALENE COMPOUNDS

(75) Inventors: Rolf Wolfgang Hartmann, Saarbrucken (DE); Bertil Wachall, St. Ingbert (DE); Makoto Yoshihama, Utsunomiya (JP); Masamichi Nakakoshi, Utsunomiya (JP); Shin Nomoto, MinamiKawachi-machi (JP); Yoshikazu Ikeda, Ishibashi-machi (JP)

(73) Assignee: Daiichi Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/866,179

(22) Filed: May 25, 2001

(65) Prior Publication Data

US 2002/0032211 A1 Mar. 14, 2002

Related U.S. Application Data

(62) Division of application No. 09/424,126, filed on Nov. 17, 1999, now abandoned.

(30) Foreign Application Priority Data

Oct. 2, 1997 (JP) .............................................. 9-284263

(51) Int. Cl.$^7$ ................... A61K 31/4409; C07D 213/24
(52) U.S. Cl. ........................ 514/277; 514/396; 546/343; 548/335.1
(58) Field of Search ....................... 546/343; 548/335.1; 514/396, 277

(56) References Cited

U.S. PATENT DOCUMENTS

| | | | |
|---|---|---|---|
| 4,540,705 A | 9/1985 | Bailey | |
| 5,807,880 A | 9/1998 | Okada et al. | ................ 514/397 |

FOREIGN PATENT DOCUMENTS

| | | |
|---|---|---|
| EP | 0 073 663 A2 | 3/1983 |
| EP | 0 125 410 A2 | 11/1984 |
| EP | 0 135 177 A2 | 3/1985 |
| EP | 0 194 580 A2 | 9/1986 |
| EP | 0 721 943 | 7/1996 |
| EP | 1 010 693 A1 | 6/2000 |
| JP | 56-081566 | 3/1981 |
| JP | 61-186348 | 8/1986 |
| JP | 6-321981 | 11/1994 |

OTHER PUBLICATIONS

Henri Christol, et al. CA55: 19875c; Acid–Catalyzed Rearrangements—(IX) dehydration of 2–phenyl–2–alkyltetralols and—indanols, cited in the European Search Report of EP98945556.3, Apr. 18, 2002.

Henri Christol, et al. CA52: 18338b; Acid–Catalyzed Rearrangements—(V) dehydration and dehydrogenation in the tetrahydronaphthalene and indane series, cited in the European Search Report of EP989455563, Apr. 18, 2002.

Mark P. Wentland, et al., synthesis and Antidepressant Properties of Novel 2–Substituted 4, –Dihydro–1H–imidazole Derivatives, Journal of Medicinal Chemistry, 1987, vol. 30 No. 8, pp. 1482–1489.

P. Perros, et al., Fragmentations induites par impact électronique de glycols–α en série tétraline, Bulletin De La Société Chimique De France 1973 No. 6 pp. 2105–2111.

Kozo Shishido, et al., Preferential Electrocyclic Reaction of o–Quinodimethane. New Route to Dihydronaphthalenes and Naphthalenes, 1987 The Chemical Society of Japan, Chemistry Letters, pp. 2113–2116.

Hans Greuter, et al. Dienol–Benzol–Umlagerung von Penta2–4–dienyl–benzocyclohexadienolen, Helvetica Chimica Acta–Vol. 56, Fasc. 7 (1973) Nr. 252–253, pp. 2479–2489 (with the International Preliminary Examination Report).

Database Chemabs Online Chemical Abstract Service, Columbus, Ohio, US; retrieved from STN Database accession No. CA61:3039H XP00216337 *CAS RN: 96978–99–3*.

David P. Kelly, et al., Non–degenerate exchange of 1,2–Dialkyl Groups in Naphthalenium Cations, Croatica Chemica Acta, 65 (3) 713–720 (1992).

CA 121:255653, Rorufu et al., 1994.

CA 118:190948, Kelly et al., 1993.

CA 109:37591, Shishido et al., 1988.

CA 102:203967, Bailey, 1985.

CA 90:70077, Grueter., 1974.

CA 92:94108, Tewari et al., 1994.

*Primary Examiner*—Jane Fan
(74) *Attorney, Agent, or Firm*—Knobbe, Martens, Olson & Bear LLP

(57) ABSTRACT

Dihydronaphthalene compounds have excellent 17α-hydroxylase/$C_{17-20}$-lyase inhibiting activity, thromboxan $A_2$ synthesis inhibiting activity, and aromatase inhibiting activity and are thereby are useful as preventive and/or therapeutic agents for various male sex hormone- and female sex hormone-dependent diseases such as prostate cancer, prostatomegaly, masculinization, breast cancer, mastopathy, uterine cancer, endometriosis, and ovarian cancer, as well as myocardial infarction, angina pectoris, and bronchial asthma.

7 Claims, No Drawings

DIHYDRONAPHTHALENE COMPOUNDS

This application is a con. of Ser. No. 09/424,126 filed Nov. 17, 1999, now abandoned.

FIELD OF THE INVENTION

The present invention relates to novel dihydronaphthalene compounds and processes for their preparation. The compounds of the present invention have excellent 17α-hydroxylase and/or $C_{17-20}$-lyase inhibiting activity, thromboxane $A_2$ synthesis inhibiting activity, and aromatase inhibiting activity, and are thereby useful as preventive and/or therapeutic agents for various male sex hormone- and female sex hormone-dependent diseases such as prostate cancer, prostatomegaly, masculinization, breast cancer, mastopathy, endometrial cancer, endometriosis, and ovarian cancer, as well as myocardial infarction, angina pectoris, and bronchial asthma.

BACKGROUND ART

As to the biosyntheses of sex steroids, which express various actions in the body, it is known that $C_{21}$ steroids, such as progesterone, are synthesized from cholesterol; further, male sex hormones such as androstenedione and testosterone, which are $C_{19}$ steroids, are synthesized by 17α-hydroxylase and/or $C_{17-20}$-lyase, and using these steroids as substrates, female sex hormones such as estrone and estradiol, which are $C_{18}$ steroids, are synthesized. Therefore, syntheses of male sex hormones and/or female sex hormones in the body can be suppressed by inhibiting these sex steroid synthesizing enzymes, i.e., 17α-hydroxylase and/or $C_{17-20}$-lyase or aromatases, which enables the prevention or treatment of diseases in which male sex hormones or female sex hormones act as exacerbating factors, such as prostate cancer, prostatomegaly, masculinization, breast cancer, mastopathy, endometrial cancer, endometriosis, and ovarian cancer.

Various findings have already shown that male sex hormone-dependent diseases such as prostate cancer and prostatomegaly can be treated by reducing male sex hormone levels in the blood. The therapeutic efficacy of reducing the level of male sex hormones by orchiectomy or adrenalectomy has been known for some times, and more recently, the efficacy of reducing the level of male sex hormones derived from gonads by the administration of an LH-RH (a pituitary hormone) agonist, has been recognized. However, the abovementioned surgical removal of organs is psychologically difficult to accept, and as well causes side effects and other disorders due to the reduction of mineral corticoids and glucocorticoids derived from the adrenal gland. Meanwhile, administration of the LH-RH agonist will inhibit syntheses of hormones derived from gonads only, but not from other organs such as adreahal gland, and even causes a temporary hormone increase known as a flare up phenomenon which is unique to agonists. On the other hand, an anti-male hormone agent to antagonize the male hormone receptor has been developed, but recently, its efficacy has been found to be diminished because of changes in the male sex hormone receptor. Against this background, a more effective male sex hormone reducing agent is desirable. In this connection, inhibition of 17α-hydroxylase and/or $C_{17-20}$-lyase is known to reduce the levels of male sex hormones to a high degree and can be expected to be highly effective in treating male sex hormone-related diseases such as prostate cancer, prostatomegaly, and masculinization. Furthermore, inhibition of 17α-hydroxylase and/or $C_{17-20}$-lyase also results in the suppression of female sex hormone syntheses.

To date, both steroid compounds and non-steroid compounds have been proposed as 17α-hydroxylase/$C_{17-20}$-lyase inhibitors. Examples of the non-steroid compounds include an imidazole derivative described in Japanese Patent Laid-open No. 64–85975 (1989), and a condensed tri-ring azole derivative described in Japanese Patent Application No. 07–510212 (1995). However, the efficacy of these compounds is not totally satisfactory and the development of compounds with higher activity has been desired.

DETAILED DESCRIPTION OF THE INVENTION

As a result of intensive study in view of the abovementioned state of affairs, the present inventors found that novel dihydronaphthalene compounds have excellent 17α-hydroxylase and/or $C_{17-20}$-lyase inhibiting activity, thromboxane $A_2$ synthesis inhibiting activity, and aromatase inhibiting activity. Namely, an objective of the present invention is to provide the novel dihydronaphthalene compounds and processes for producing the same.

The present invention relates to the novel dihydronaphthalene compounds and processes for producing the same. The compounds according to the present invention have excellent 17α-hydroxylase and/or $C_{17-20}$-lyase inhibiting activity, thromboxane $A_2$ synthesis inhibiting activity, and aromatase inhibiting activity, and are thus useful as preventive and/or therapeutic agents for various male sex hormone- and female sex hormone-dependent diseases, such as prostate cancer, prostatomegaly, masculinization, breast cancer, mastopathy, endometrial cancer, endometriosis, and ovarian cancer, as well as myocardial infarction, angina pectoris, and bronchial asthma.

The present invention relates to novel dihydronaphthalene compounds of the following general formula (1)

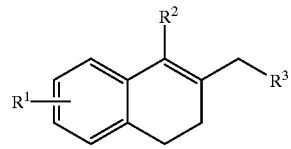

wherein $R^1$ represents hydrogen, hydroxyl, or alkyloxy, $R^2$ represents lower alkyl, aralkyl, or phenyl, and $R^3$ represents alkyl, phenyl, pyridyl, or imidazolyl.

More specifically, examples of the novel dihydronaphthalene compounds according to the present invention of general formula (1) include (1) 3-[(1-methyl-3,4-dihydro-2-naphthalenyl)methyl]pyridine, (2) 3-[(5-methoxy-1-methyl-3,4-dihydro-2-naphthalenyl)methyl]pyridine, (3) 3-[(6-methoxy-1-methyl-3,4-dihydro-2-naphthalenyl)methyl]pyridine, (4) 3-[(7-methoxy-1-methyl-3,4-dihydro-2-naphthalenyl)methyl]pyridine, (5) 5-methyl-6-(3-pyridylmethyl)-7,8-dihydro-1-naphthalenol, (6) 5-methyl-6-(3-pyridylmethyl)-7,8-dihydro-2-naphthalenol, (7) 8-methyl-7-(3-pyridylmethyl)-5,6-dihydro-2-naphthalenol, (8) 4-[(1-methyl-3,4-dihydro-2-naphthalenyl)methyl]pyridine, (9) 4-[(5-methoxy-1-methyl-3,4-dihydro-2-naphthalenyl)methyl]pyridine,

(10) 4-[(6-methoxy-1-methyl-3,4-dihydro-2-naphthalenyl) methyl]pyridine,
(11) 4-[(7-methoxy-1-methyl-3,4-dihydro-2-naphthalenyl) methyl]pyridine,
(12) 5-methyl-6-(4-pyridylmethyl)-7,8-dihydro-1-naphthalenol,
(13) 5-methyl-6-(4-pyridylmethyl)-7,8-dihydro-2-naphthalenol,
(14) 8-methyl-7-(4-pyridylmethyl)-5,6-dihydro-2-naphthalenol,
(15) 4-[(1-ethyl-5-methoxy-3,4-dihydro-2-naphthalenyl) methyl]pyridine,
(16) 4-[(1-ethyl-6-methoxy-3,4-dihydro-2-naphthalenyl) methyl]pyridine,
(17) 4-[(1-ethyl-7-methoxy-3,4-dihydro-2-naphthalenyl) methyl]pyridine,
(18) 4-[(6-methoxy-1-methyl-3,4-dihydro-2-naphthalenyl) methyl]-1H-imidazole,
(19) 4-[(5-methoxy-3,4-dihydro-2-naphthalenyl)methyl] pyridine,
(20) 4-[(6-methoxy-3,4-dihydro-2-naphthalenyl)methyl] pyridine,
(21) 4-[(7-methoxy-3,4-dihydro-2-naphthalenyl)methyl] pyridine,
(22) 4-[(6-methoxy-1-propyl-3,4-dihydro-2-naphthalenyl) methyl]pyridine hydrochloride,
(23) 6-(4-pyridylmethyl)-7,8-dihydro-2-naphthalenol,
(24) 2-(1H-4-imidazolylmethyl)-6-methoxy-3,4-dihydronaphthalene hydrochloride,
(25) 4-[(7-methoxy-1-methyl-3,4-dihydro-2-naphthalenyl) methyl]-1H-imidazole,
(26) 4-[(5-methoxy-1-methyl-3,4-dihydro-2-naphthalenyl) methyl]-1H-imidazole,
(27) 4-[(1-ethyl-6-methoxy-3,4-dihydro-2-naphthalenyl) methyl]-1H-imidazole,
(28) 4-[(1-ethyl-7-methoxy-3,4-dihydro-2-naphthalenyl) methyl]-1H-imidazole,
(29) 4-[(1-ethyl-5-methoxy-3,4-dihydro-2-naphthalenyl) methyl]-1H-imidazole, hydrochloride,
(30) 4-[(6-methoxy-1-propyl-3,4-dihydro-2-naphthalenyl) methyl]-1H-imidazole,
(31) 4-[(5-methoxy-1-propyl-3,4-dihydro-2-naphthalenyl) methyl]-1H-imidazole,
(32) 4-[(6-methoxy-1-phenyl-3,4-dihydro-2-naphthalenyl) methyl]-1H-imidazole,
(33) 4-[(7-methoxy-1-phenyl-3,4-dihydro-2-naphthalenyl) methyl]-1H-imidazole,
(34) 4-[(5-methoxy-1-phenyl-3,4-dihydro-2-naphthalenyl) methyl]-1H-imidazole,
(35) 4-[(1-benzyl-6-methoxy-3,4-dihydro-2-naphthalenyl) methyl]-1H-imidazole,
(36) 4-[(5-methoxy-3,4-dihydro-2-naphthalenyl)methyl]-1H-imidazole hydrochloride,
(37) 4-[(7-methoxy-3,4-dihydro-2-naphthalenyl)methyl]-1H-imidazole,
(38) 4-[(5-ethoxy-1-methyl-3,4-dihydro-2-naphthalenyl) methyl]-1H-imidazole,
(39) 4-[(6-ethoxy-1-methyl-3,4-dihydro-2-naphthalenyl) methyl]-1H-imidazole,
(40) 4-[(7-ethoxy-1-methyl-3,4-dihydro-2-naphthalenyl) methyl]-1H-imidazole,
(41) 4-[(1-methyl-6-propoxy-3,4-dihydro-2-naphthalenyl) methyl]-1H-imidazole,
(42) 4-[(1-methyl-6-isobutoxy-3,4-dihydro-2-naphthalenyl) methyl]-1H-imidazole.

The compounds of the present invention include, in addition to the abovementioned compounds, stereoisomers, and acid or base salts of these compounds. Examples of acids to form acid addition salts include inorganic acids such as hydrochloric acid, hydrobromic acid, hydriodic acid, sulfuric acid, nitric acid, and phosphoric acid, and organic acids such as formic acid, acetic acid, propionic acid, oxalic acid, malonic acid, succinic acid, fumaric acid, maleic acid, lactic acid, malic acid, citric acid, tartaric acid, carbonic acid, picric acid, methanesulfonic acid, and glutamic acid. Examples of bases to form base salts include inorganic bases such as sodium, potassium, magnesium, calcium, and aluminum, organic bases such as lower alkyl amines, lower alcohol amines, basic amino acids such as lysine, arginine, and ornithine, and ammonium. Furthermore, hydrates and solvates with lower alcohols and other solvents may also be formed.

The compounds of the present invention can be produced by the following method. Briefly, a 1-tetralone compound with a hydrogen or alkoxyl group is heated with pyridylcarbaldehyde which has a 3- or 4-pyridyl group, or 1H-imidazole-4-carbaldehyde under acidic conditions. The resulting substituted 1-tetralone is reduced using an appropriate reducing agent, and the reduced compound is then treated with an appropriate Grignard reagent or reduced with hydride, followed by dehydration to obtain the target compound of the present invention, i.e., a dihydronaphthalene compound. Further, a dihydronaphthalene compound having a hydroxyl group can be obtained by purification with, for example, boron tribromide. The reactions above are shown in the following scheme:

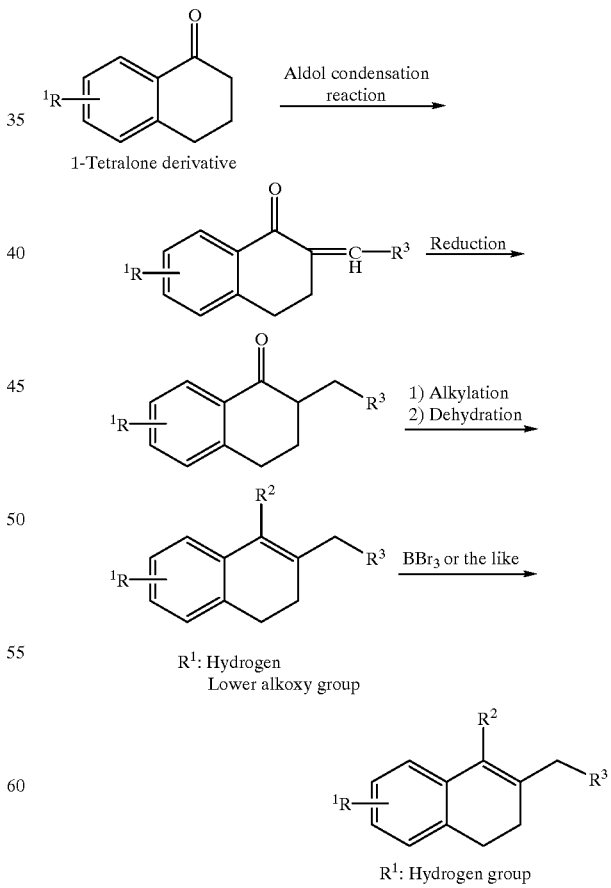

The compounds of the present invention can be safely administered orally or parenterally as pharmaceutical preparations to humans and other animals. Methods of parenteral administration include intravenous injection, intramuscular injection, cutaneous injection, intraperitoneal injection, transdermal administration, transpulmonary administration, nasal administration, transenteral administration, intraoral administration, and transmucous administration. Examples of parenteral preparations include injectables, suppositories, aerosols and percutaneous absorbing tapes. Examples of preparations for oral administration include tablets (including sugar coated tablets, coated tablets and buccal tablets), dispersible powders, capsules (including soft capsules), granules (including coated granules), pills, troches, liquids, and pharmaceutically acceptable slow-releasing forms of the above. Examples of liquid compositions for oral administration include suspensions, emulsions, syrups (including dry syrups), and elixirs.

These preparations are produced as medicinal compositions together with pharmacologically acceptable carriers, excipients, disintegrating agents, lubricants, coloring agents, or the like according to known pharmaceutical production methods. Examples of carriers or excipients to be used for these preparations include lactose, glucose, sucrose, mannitol, potato starch, corn starch, calcium carbonate, calcium phosphate, calcium sulfate, crystalline cellulose, licorice powder, and gentiana powder. Examples of binding agents include starch, gum tragacanth, gelatin, syrup, polyvinyl alcohol, polyvinyl ether, polyvinylpyrrolidone, hydroxypropylcellulose, methylcellulose, ethylcellulose, and carboxymethylcellulose. Examples of disintegrating agents include starch, agar, gelatin powder, sodium carboxymethylcellulose, calcium carboxymethylcellulose, crystalline cellulose, calcium carbonate, sodium hydrogencarbonate, and sodium alginate. Examples of lubricating agents include magnesium stearate, talc, hydrogenated vegetable oils, and macrogol. Pharmaceutically acceptable coloring agents can be used.

Tablets and granules may be coated, if necessary, with sucrose, gelatin, hydroxypropylcellulose, purified shellac, gelatin, glycerine, sorbitol, ethylcellulose, hydroxypropylcellulose, hydroxypropylmethylcellulose, polyvinylpyrrolidone, cellulose acetate phthalate, hydroxypropylmethylcellulose phthalate, methyl methacrylate, methacrylic acid polymers, or the like, or with a layer of combination of two or more of these coating materials. Capsules made of ethylcellulose, gelatin or the like can also be used. Injectable agents can be prepared, if necessary, by adding pH controlling agents, buffering agents, stabilizers, solubilizing agents, or the like, according to the customary method.

The dosage of the compound of the present invention is not particularly restricted and would vary as a function of the severity of the condition to be treated, the age, health, and body weight of the patient, and other factors. A proposed dosage of 1–1000 mg, preferably 50–200 mg, per day for adult may be administered orally or parenterally once or several times a day.

EXAMPLES

The present invention is explained in greater detail by the following examples which are for purposes of illustration only and are not intended to define the limits of the invention.

Example 1

Preparation of Compounds of the Present Invention:

The compounds of Production Examples 1 to 5 were synthesized as follows: To 90 ml of 54% sulfuric acid were added 7.5 g (60 mmol) of pyridylcarbaldehyde and 50 mmol of a tetralone compound, and the admixture was heated at 80° C. for 1 hour. The reaction solution was cooled in ice and the resulting precipitate of sulfate crystals was filtered, neutralized with 1 L of an aqueous saturated sodium hydrogencarbonate solution, then washed with water by filtration. The yellow crystals so obtained were dried over silica, then fractionated by column chromatography and/or recrystallized with an appropriate solvent to obtain the target compound.

Example 2

Preparation of Compounds of the Present Invention:

The compounds of Production Examples 6 and 7 were synthesized as follows: To 105 ml of 89% phosphoric acid were added 11.0 g (103 mmol) of pyridylcarbaldehyde and 70 mmol of a tetralone compound, and the admixture was heated at 80° C. for 4 hours. The reaction solution was cooled in ice, the resulting precipitate was filtered, then neutralized with an aqueous saturated sodium hydrogencarbonate solution (0.7 L), and the resulting crystals were washed with water by filtration. The pale yellow crystals so obtained were dried over silica and recrystallized with ethyl acetate to obtain the target compound.

Example 3

Preparation of Compounds of the Present Invention:

The compounds of Production Examples 8 to 14 were synthesized as follows: In 250 ml of ethanol were suspended 34 mmol of an unsaturated ketone compound obtained by the method of Example 1 or 2 above (a compound of one of Production Examples 1 to 7). To this suspension were added 0.5 g of 10% Pd—C and 10 ml of 0.2 N hydrochloric acid, and the admixture was stirred under a hydrogen flow for 18 hours. After removing the catalyst by filtration, dehydrating with anhydrous sodium sulfate, and concentrating the solvent, a residue containing the target compound was obtained. The residue was subjected to silica gel column chromatography (eluting with ethyl acetate or petroleum ether:acetone=6:4) to elute the target compound or recrystallized with an appropriate solvent to obtain the target compound as crystals.

Example 4

Preparation of Compounds of the Present Invention:

The compounds of Production Examples 15 to 22 were synthesized as follows: To a methyl magnesium iodide solution, which was prepared by adding 1.56 g (64 mmol) of magnesium pieces and 3.9 ml (63 mmol) of methyl iodide to 50 ml of anhydrous ether, were added dropwise 70 ml of an anhydrous tetrahydrofuran (THF) solution containing 25 mmol of a saturated ketone compound obtained by the method of Example 3 above (a compound of one of Production Examples 8 to 14). The admixture was refluxed for 18 hours, poured into 50 g of ice water, and heated at 70° C. for 2 hours with 65 ml of 25% sulfuric acid. This reaction solution was alkalinized with sodium hydroxide while cooling. The resulting suspension was extracted several times with diethyl ether, then the organic layer was dehydrated with anhydrous sodium sulfate and concentrated under vacuum. The concentrate was purified by silica gel column chromatography (eluting with petroleum ether:acetone= 6:4), and the resulting pale yellow oily substance was allowed to stand at 4° C. for 8 days to obtain the target compound as crystals.

Example 5
Preparation of Compounds of the Present Invention:

The compounds of Production Examples 23 to 28 were synthesized as follows: A solution of anhydrous methylene chloride (90 ml) containing 3 mmol of an alkyloxy compound (a compound of one of Production Examples 15 to 22) obtained by the method of Example 4 above was cooled to −78° C., and 1 ml (10 mmol) of boron tribromide was added dropwise to this solution under a nitrogen flow. The solution was stirred at −78° C. for about 30 minutes, then at room temperature for 4 hours, after which 3 ml of methanol were added dropwise. This reaction solution was concentrated to one fourth of the original volume and the hydrobromic acid salt so produced was filtered. The resulting precipitate was dissolved in 1 N sulfuric acid and neutralized with a saturated sodium hydrogencarbonate solution. In the case where no hydrobromic acid salt was precipitated, the solution was concentrated to dryness, the resulting oily substance was suspended in 1 N sulfuric acid, and this sulfuric acid suspension was neutralized with a saturated sodium hydrogencarbonate solution. The resulting precipitate was filtered and washed with an appropriate solvent to obtain the target compound.

Example 6
Preparation of Compounds of the Present Invention:

The compounds of Production Examples 29, 30 and 32 were synthesized as follows: To 90 ml of a 50% sulfuric acid solution were added 60 mmol of allylcarbaldehyde and 50 mmol of a tetralone compound, and the admixture was heated at 80° C. for 1 hour. This solution was cooled in ice and filtered, and the resulting sulfate crystals were dissolved or suspended in 1 L of water, after which the solution or suspension was neutralized with saturated sodium hydrogencarbonate. The yellow precipitate so produced was filtered, washed with water, then dried over silica. This precipitate was subjected to column chromatography (eluting with diethyl ether) and a fraction containing the target compound was crystallized using an appropriate solvent to obtain the target compound as crystals.

Example 7
Preparation of Compounds of the Present Invention:

The compounds of Production Example 31 was synthesized as follows: To 105 ml of an 89% phosphoric acid solution were added 11.0 g (103 mmol) of pyridylcarbaldehyde and 70 mmol of a tetralone compound, and the admixture was heated at 80° C. for 4 hours. This solution was cooled in ice and the resulting precipitate of phosphate crystals was filtered, dissolved in 0.7 L of water, then neutralized with aqueous saturated sodium hydrogencarbonate solution. The pale yellow precipitate was filtered, washed with water and dried over silica. The resulting crude crystals were recrystallized with ethyl ether to obtain the target compound.

Example 8
Preparation of Compounds of the Present Invention:

The compounds of Production Examples 33 to 36 were synthesized as follows: To 250 ml of ethanol were suspended 34 mmol of an unsaturated ketone compound obtained by the method of Example 6 or 7 (a compound of one of Production Examples 29 to 32). To this suspension were added 0.5 g of 10% Pd—C and 10 ml of 0.2 N hydrochloric acid, and the admixture was stirred under a hydrogen flow for 18 hours. After removing the catalyst by filtration, dehydrating with anhydrous sodium sulfate, and concentrating under vacuum, the target compound was obtained by fractionation by silica gel column chromatography or by crystallization with an appropriate solvent.

Example 9
Preparation of Compounds of the Present Invention:

The compounds of Production Examples 37 to 41, 43, 44 and 46 were synthesized as follows: To an alkyl magnesium halide solution, which was prepared by adding 1.56 g (64 mmol) of magnesium and 63 mmol of alkyl halide to 50 ml of anhydrous ether, were added dropwise 70 ml of an anhydrous tetrahydrofuran (THF) solution containing 25 mmol of a saturated ketone compound (a compound of one of Production Examples 33 to 36) obtained by the method of Example 8. The admixture was refluxed for 18 hours, poured onto 50 g of ice, and heated at 70° C. for 2 hours with 65 ml of 25% sulfuric acid. This reaction solution was alkalinized with sodium hydroxide while cooling. The resulting suspension was extracted several times with diethyl ether for a pyridine derivative or with dichloromethane:ethanol=9:1 for an imidazole derivative, then the organic layer was dehydrated with anhydrous sodium sulfate and concentrated under vacuum. The residue obtained was fractionated by silica gel column chromatography, and the resulting pale colored oily substance was allowed to stand at 4° C. for 8 days to obtain the target compound as crystals.

The compound of Production Example 44 was obtained as follows: One gram of the pale colored oily substance obtained as above was dissolved in 200 ml of ether/acetone. To this solution were added 2 to 3 ml of a hydrochloric acid/ether solution prepared by adding 2 ml of a hydrochloric/acid solution (prepared first by adding 3 ml of conc. hydrochloric acid to 50 ml of ether) to 20 ml of ether. The admixture was stirred, then the precipitated hydrochloride was filtered. This hydrochloride was washed with a small amount of ether and then dried under vacuum to obtain the target compound.

Further, the compounds in Production Examples 37 to 39 and 46, which relate to unsubstituted compounds in Production Examples 41 to 43, were isolated as byproducts by column chromatography.

Compounds to be used for production in Production Examples 37 and 39 were obtained as follows: 3,4-Dihydronaphthalene-1-ethyl and a related ethylidene-tetrahydronaphthalene compound were mixed in a 1:1 ratio and the admixture was further reacted for purification. To induce double bond isomerization, 0.4 g of the admixture was heated in a solution of 0.36 g of p-toluenesulfonic acid (2.1 mmol) in 20 ml acetic acid at 90° C. for 24 hours. This reaction solution was alkalinized with an aqueous saturated sodium hydrogencarbonate and sodium carbonate and extracted 3 times with ethyl ether. The organic layer was dehydrated over anhydrous sodium sulfate and concentrated under vacuum. The concentrate was purified by column chromatography to obtain the target compound.

Example 10
Preparation of Compounds of the Present Invention:

The compound of Production Example 45 was synthesized as follows: A solution of anhydrous methylene chloride (90 ml) containing 3 mmol of the methoxy compound obtained by the method of Example 9 was cooled at −78° C., and 1 ml of boron tribromide was added dropwise to this solution under a nitrogen flow. The solution was stirred at −78° C. for 30 minutes, then at room temperature for 4 hours, after which 3 ml of methanol were added dropwise.

This reaction solution was concentrated to one fourth of its original volume, then the resulting hydrobromide was filtered and dissolved in 1 N sulfuric acid, and the solution was neutralized with a saturated sodium hydrogencarbonate solution. In the case where no hydrobromide was deposited, the solution was concentrated and the resulting oily substance was suspended in 1 N sulfuric acid. This sulfuric acid suspension was neutralized with a saturated sodium hydrogen carbonate solution. The resulting precipitate containing the target compound was filtered and washed with an appropriate solvent to obtain the target compound.

Example 11
Preparation of Compounds of the Present Invention:

The compounds of Production Examples 42 and 46 were synthesized as follows: To 10 mmol of the saturated ketone compound obtained by the method of Example 8 dissolved in 65 ml of methanol were added gradually 378 mg (10 mmol) of sodium boron hydride while cooling on ice so as to keep the temperature below 15° C. After stirring for 2.5 hours, the reaction solution was added to 100 ml of ice water, and heated at 70° C. for 1 hour with 50 ml of 25% sulfuric acid. This solution was alkalinized with sodium hydroxide while cooling in ice.

The suspension so obtained was extracted several times with diethyl ether for a pyridine derivative, or with dichloromethane:ethanol=9:1 for an imidazole derivative. The organic layer was dried over anhydrous sodium sulfate and concentrated under vacuum. The residue so obtained was fractionated by silica gel column chromatography to obtain a fraction containing the target compound, from which an oily substance was obtained after concentration under vacuum. The compound of Production Example 42 was obtained as crystals by allowing the oily substance to stand at 4° C. for 8 days. To prepare the compound of Production Example 46, 1 g of the abovementioned oily substance was dissolved in 200 ml of ether/acetone. To this solution were added 2 to 3 ml of a hydrochloric acid/ether solution prepared by adding 2 ml of a hydrochloric/acid solution (prepared first by adding 3 ml of conc. hydrochloric acid to 50 ml of ether) to 20 ml of ether. After stirring, the deposited hydrochloride was filtered, washed with a small amount of ether, then dried under vacuum to obtain the target compound.

Example 12
Preparation of Compounds of the Present Invention:

The compound of Production Example 47 was synthesized as follows: To 90 ml of 54% sulfuric acid were added 60 mmol of 1H-imidazolyl-4-carbaldehyde and 50 mmol of the corresponding tetralone compound, and the admixture was heated at 80° C. for 3 hours. This reaction solution was cooled in ice, and the precipitated sulfate was filtered, neutralized with 1 L of an aqueous saturated sodium hydrogencarbonate solution, filtered again, washed with water, then dried over silica. The residue so obtained was recrystallized with an appropriate solvent to obtain the target compound.

Example 13
Preparation of Compounds of the Present Invention:

The compound of Production Example 48 was synthesized as follows: To 250 ml of ethanol were suspended 34 mmol of an unsaturated ketone compound obtained in Example 12 above. To this suspension were added 0.5 g of 10% Pd—C and 10 ml of 0.2 N hydrochloric acid, and the admixture was stirred under a hydrogen flow for 18 hours. After removing the catalyst by filtration, dehydrating with anhydrous sodium sulfate, and concentrating the solvent, the resulting residue was recrystallized with an appropriate solvent to obtain the target compound as crystals.

Example 14
Preparation of Compounds of the Present Invention:

The compound of Production Example 49 was synthesized as follows: To a methyl magnesium iodide solution, which was prepared by adding 1.56 g (64 mmol) of magnesium and 3.9 ml (63 mmol) of methyl iodide to 50 ml of anhydrous ether, were added dropwise 70 ml of an anhydrous tetrahydrofuran (THF) solution or suspension containing 25 mmol of a saturated ketone compound obtained by the method of Example 13. The admixture was refluxed for 18 hours, poured into 50 g of ice water, and heated at 70° C. for 2 hours with 65 ml of 25% sulfuric acid. This reaction mixture was alkalinized with sodium hydroxide while cooling. The resulting suspension was extracted several times with dichloromethane:ethanol=9:1, and the organic layer was dehydrated with anhydrous calcium chloride and concentrated under vacuum. The concentrate was fractionated by column chromatography, and the fraction containing the target compound was recrystallized with an appropriate solvent to obtain the target compound.

Example 15
Preparation of Compounds of the Present Invention:

The compounds of Production Examples 50, 64, 66, 68, 73 and 76 were synthesized as follows: To 90 ml of 50% sulfuric acid were added 60 mmol of 1H-imidazolyl-4-carbaldehyde and 50 mmol of a corresponding tetralone compound, and the admixture was heated at 80° C. for 2 hours while stirring. This reaction solution was cooled in ice and, the precipitated sulfate was filtered and neutralized with 1 L of an aqueous saturated sodium hydrogencarbonate solution. The resulting crystals were filtered, washed with water, then dried over silica to obtain the target compound.

Example 16
Preparation of Compounds of the Present Invention:

The compounds of Production Examples 51, 65, 67, 69, 74 and 77 were synthesized as follows: To 250 ml of ethanol were suspended 34 mmol of an unsaturated ketone compound obtained in Example 15 above. To this suspension were added 0.5 g of 10% Pd—C and 10 ml of 0.2 N hydrochloric acid, and the admixture was stirred under a hydrogen flow for 18 hours. After removing the catalyst by filtration and concentrating the solvent, the resulting residue was alkalinized with aqueous saturated sodium hydrogencarbonate and extracted with 2-butanone. The organic layer was washed with a saturated sodium chloride solution and dehydrated with anhydrous magnesium sulfate. After concentrating the solvent under vacuum, the resulting residue was recrystallized with an appropriate solvent to obtain the target compound as crystals.

Example 17
Preparation of Compounds of the Present Invention:

The compounds of Production Examples 52 to 57, 62, 63, 70 to 72, 75 and 77 were synthesized as follows: To an alkyl magnesium halide solution, which was prepared by adding 0.48 g (20 mmol) of magnesium and 20 mmol of alkyl halide to 17 ml of anhydrous ether, were added dropwise 50 ml of anhydrous tetrahydrofuran (THF) solution containing 7.8 mmol of saturated ketone compound obtained by the method of Example 8, 13 or 18. The admixture was refluxed for 18 hours, poured into 15 g of ice water, and heated at 70° C. for 2 hours with 24 ml of 25% sulfuric acid. This reaction solution was alkalinized with sodium hydroxide while cooling. The resulting suspension was extracted several times with ethyl acetate, the organic layer was washed with water and a saturated sodium chloride solution, then dehydrated with anhydrous magnesium sulfate, after which the solvent was concentrated under vacuum. The residue so obtained was fractionated by column chromatography with NH silica gel (Fuji Silicia), and the fraction containing the target compound was recrystallized with an appropriate solvent to obtain the target compound.

The compounds of Production Examples 62 and 63 were isolated as byproducts during the purification of Compounds in Production Examples of 55 and 54.

The compounds of Production Examples of 55, 66 and 71 were obtained as hydrochloride crystals by dissolving the abovementioned colorless to brown oily substance isolated by column chromatography in 2 ml ethanol, adding saturated hydrochloride-saturated diethyl ether (3 ml) while cooling in ice, then filtrating crystals so formed.

Example 18
Preparation of Compounds of the Present Invention:

The compounds of Production Examples 58 to 60 were synthesized as follows: To an phenyl magnesium bromide solution, which was prepared by adding 0.48 g (20 mmol) of magnesium and 2.1 ml (20 mmol) of bromobenzene to 17 ml of anhydrous ether, were added dropwise 50 ml of anhydrous tetrahydrofuran (THF) solution or suspension containing 7.8 mmol of saturated ketone compound obtained by the method of Example 8, 13 or 16. The admixture was refluxed for 18 hours, poured into 15 g of ice water, and heated at 70° C. for 2 hours with 24 ml of 25% sulfuric acid. This reaction solution was alkalinized with sodium hydroxide while cooling. The resulting suspension was extracted several times with ethyl acetate, the organic layer was washed with water and a saturated sodium chloride solution, then dehydrated with anhydrous magnesium sulfate, and the solvent was concentrated under vacuum. The residue so obtained was fractionated by column chromatography with NH silica gel (Fuji Silicia), and the fraction containing the target composition was recrystallized with an appropriate solvent to obtain the target compound.

Example 19
Preparation of Compounds of the Present Invention:

The compound of Production Example 61 was synthesized as follows: A benzyl magnesium bromide solution, which was prepared by adding 0.72 g (30 mmol) of magnesium pieces and 3.6 ml (30 mmol) of benzyl bromide to 26 ml of anhydrous ether, was added dropwise to 80 ml of anhydrous tetrahydrofuran (THF) solution or suspension containing 12 mmol of saturated ketone compound obtained by the method of Example 8. The admixture was refluxed for 18 hours, poured into 30 g of ice water, and heated at 70° C. for 2 hours with 35 ml of 25% sulfuric acid. This reaction solution was alkalinized with sodium hydroxide while cooling. The resulting suspension was extracted several times with ethyl acetate, the organic layer was washed with water and saturated sodium chloride solution and dehydrated with anhydrous magnesium sulfate, after which the solvent was concentrated under vacuum. The residue so obtained was fractionated by column chromatography with NH silica gel (Fuji Silicia), and the fraction containing the target compound was recrystallized with ethyl acetate/hexane to obtain the target compound.

Production Example 1
Production of 2-[1-(3-pyridyl)methylidene]-1,2,3,4-tetrahydro-1-naphthalenone:

The title compound was produced from 1-tetralone and pyridine-3-carbaldehyde by the method of Example 1.

Form: Pale yellow crystals
Yield: 80%
Melting point: 76.5–77.5° C.
$^1$H-NMR (80 MHz, CDCl$_3$) δ (ppm): 2.73–3.28 (m, 4H); 7.14–7.84 (m, 6H); 7.89–8.21 (m, 1H); 8.42–8.79 (m, 2H)
IR (cm$^{-1}$): 3045, 3015, 2930, 2880, 1660, 1600, 1590, 1410, 1290, 1020, 950, 740, 710

Production Example 2
Production of 5-methoxy-2-[1-(3-pyridyl)methylidene]-1,2,3,4-tetrahydro-1-naphthalenone:

The title compound was produced from 5-methoxy-1-tetralone and pyridine-3-carbaldehyde by the method of Example 1.

Form: Yellow crystals
Yield: 74%
Melting point: 106–108° C.
$^1$H-NMR (80 MHz, CDCl$_3$) δ (ppm): 2.71–3.22 (m, 4H); 3.85 (s, 3H) 6.91–7.47 (m, 3H); 7.60–7.88 (m, 3H); 8.47–8.76 (m, 2H)
IR (cm$^{-1}$): 3000, 2960, 2820, 1660, 1580, 1420, 1260, 1025, 740, 705

Production Example 3
Production of 7-methoxy-2-[1-(3-pyridyl)methylidene]-1,2,3,4-tetrahydro-1-naphthalenone:

The title compound was produced from 7-methoxy-1-tetralone and pyridine-3-carbaldehyde by the method of Example 1.

Form: Yellow crystals
Yield: 88%
Melting point: 102.5–104° C.
$^1$H-NMR (400 MHz, CDCl$_3$) δ (ppm): 2.90–2.94 (m, 2H); 3.08–3.11 (m, 2H); 3.88 (s, 3H); 7.09 (dd, 1H); 7.18 (d, 1H); 7.36 (dd, 1H); 7.79 (s, 1H); 8.57 (dd, 1H); 8.58 (s, 1H)
IR (cm$^{-1}$): 3010, 2930, 2830, 1665, 1605, 1490, 1395, 1020, 910, 735, 710

Production Example 4
Production of 5-methoxy-2-[1-(4-pyridyl)methylidene]-1,2,3,4-tetrahydro-1-naphthalenone:

The title compound was produced from 5-methoxy-1-tetralone and pyridine-4-carbaldehyde by the method of Example 1.

Form: Brown crystals
Yield: 60%
Melting point: 144–145° C.
$^1$H-NMR (80 MHz, CDCl$_3$) δ (ppm): 2.78–3.20 (m, 4H); 3.86 (s, 3H); 6.97–7.47 (m, 4H); 7.58–7.86 (m, 2H); 8.62 (dd, 2H)
IR (cm$^{-1}$): 3000, 2950, 2820, 1660, 1600, 1590, 1475, 1265, 1025, 970, 750, 535

Production Example 5
Production of 7-methoxy-2-[1-(4-pyridyl)methylidene]-1,2,3,4-tetrahydro-1-naphthalenone:

The title compound was produced from 7-methoxy-1-tetralone and pyridine-4-carbaldehyde by the method of Example 1.

Form: Pale yellow crystals
Yield: 84%
Melting point: 134.5–135° C.
$^1$H-NMR (400 MHz, CDCl$_3$) δ (ppm): 2.90–3.06 (m, 2H); 3.07–3.09 (m, 2H); 3.88 (s, 3H); 7.09–7.11 (m, 1H); 7.18–7.20 (m, 1H); 7.28(2H); 7.61(d, 1H); 7.72(s, 1H); 8.67(dd, 2H)
IR (cm$^{-1}$): 3060, 3020, 2960, 2900, 2830, 1660, 1590, 1490, 1320, 1255, 1030, 830, 750, 530

Production Example 6

Production of 6-methoxy-2-[1-(3-pyridyl)methylidene]-1,2,3,4-tetrahydro-1-naphthalenone:

The title compound was produced from 6-methoxy-1-tetralone and pyridine-3-carbaldehyde by the method of Example 2.

Form: White crystals
Yield: 84%
Melting point: 106.5–107° C.
$^1$H-NMR (400 MHz, CDCl$_3$) δ (ppm): 2.93–2.96 (m, 2H); 3.08–3.11 (m, 2H); 3.88 (s, 3H); 6.72 (d, 1H); 6.89 (dd, 1H); 7.35(dd, 1H); 7.72(d, 1H); 7.76(s, 1H); 8.12(d, 1H); 8.57 (dd, 1H); 8.68(s, 1H)
IR (cm$^{-1}$): 3000, 2930, 2820, 1660, 1610, 1590, 1480, 1335, 1265, 1025, 950, 850

Production Example 7

Production of 6-methoxy-2-[1-(4-pyridyl)methylidene]-1,2,3,4-tetrahydro-1-naphthalenone:

The title compound was produced from 6-methoxy-1-tetralone and pyridine-4-carbaldehyde by the method of Example 2.

Form: Pale yellow crystals
Yield: 78%
Melting point: 127.5–128.5° C.
$^1$H-NMR (400 MHz, CDCl$_3$) δ (ppm): 2.93–2.96 (m, 2H); 3.05–3.09 (m, 2H); 3.88 (s, 3H); 6.71 (d, 1H); 6.89 (dd, 1H); 7.27 (d, 2H); 7.70 (s, 1H); 8.12 (d, 1H); 8.66 (d, 2H)
IR (cm$^{-1}$): 3020, 2970, 2840, 1665, 1600, 1590, 1490, 1325, 1275, 1140, 950

Production Example 8

Production of 2-(3-pyridylmethyl)-1,2,3,4-tetrahydro-1-naphthalenone:

The title compound was produced from the compound of Production Example 1 by the method of Example 3.

Form: White crystals
Yield: 83%
Melting point: 45–46.5° C.
$^1$H-NMR (80 MHz, CDCl$_3$) δ (ppm) 1.41–2.40 (m, 4H); 2.45–3.13 (m, 4H); 3.17–3.66 (m, 1H); 6.80–7.70 (m, 5H); 7.93–8.21 (m, 1H) 8.34–8.63 (m, 2H)
IR (cm$^{-1}$) 3020, 2920, 2860, 1670, 1600, 1575, 1440, 1225, 1025, 750, 720

Production Example 9

Production of 5-methoxy-2-(3-pyridylmethyl)-1,2,3,4-tetrahydro-1-naphthalenone:

The title compound was produced from the compound of Production Example 2 by the method of Example 3.

Form: Pale red crystals
Yield: 88%
Melting point: 76.5–78° C.
$^1$H-NMR (400 MHz, CDCl$_3$) δ (ppm): 1.73–1.79, 2.10–2.15 (m, 2H); 2.61–2.7 6, 3.06–3.12 (m, 4H); 3.38–3.42 (m, 1H); 3.86 (s, 3H); 7.01–7.03, 7.57–7.60 (m, 2H); 7.21–7.31 (m, 2H); 7.66 (d, 1H); 8.46–8.50 (m, 2H)
IR (cm$^{-1}$): 3060, 3010, 2950, 2910, 2820, 1680, 1595, 1580, 1420, 1260, 1040, 950, 745, 710

Production Example 10

Production of 6-methoxy-2-(3-pyridylmethyl)-1,2,3,4-tetrahydro-1-naphthalenone:

The title compound was produced from the compound of Production Example 6 by the method of Example 3.

Form: Brown crystals
Yield: 73%
Melting point: 61.5–62° C.
$^1$H-NMR (400 MHz, CDCl$_3$) δ (ppm): 1.75–1.81, 2.05–2.10 (m, 2H) 2.68–2.73 (m, 2H); 2.90–2.93 (m, 2H); 3.43–3.45 (m, 1H); 3.84 (s, 3H) 6.67 (d, 1H);6.83 (dd); 7.21–7.26 (m, 1H); 7.58 (d, 1H); 8.03 (d, 1H); 8.46–8.50 (m, 2H)
IR (cm$^{-1}$): 3040, 3020, 2940, 2910, 2820, 1660, 1600, 1420, 1260, 1250, 1020, 930, 855, 710

Production Example 11

Production of 7-methoxy-2-(3-pyridylmethyl)-1,2,3,4-tetrahydro-1-naphthalenone:

The title compound was produced from the compound of Production Example 3 by the method of Example 3.

Form: Brown crystals
Yield: 77%
Melting point: 69.5–70° C.
$^1$H-NMR (400 MHz, CDCl$_3$) δ (ppm):1.76–1.84, 2.07–2.12 (each m, 2H) 2.71–2.78 (m, 2H); 2.88–2.91 (m, 2H); 3.39–3.46 (m, 1H); 3.84 (s, 3H) 7.06 (dd, 1H); 7.14 (d, 1H); 7.22–7.26 (m, 1H); 7.53 (d, 1H); 7.57–7.60 (m, 1H); 8.47–8.50 (m, 2H).
IR (cm$^{-1}$): 3100, 3080, 3060, 2970, 2880, 2850, 1685, 1620, 1510, 1435, 1260, 1040, 745, 730, 560

Production Example 12

Production of 5-methoxy-2-(4-pyridylmethyl)-1,2,3,4-tetrahydro-1-naphthalenone:

The title compound was produced from the compound of Production Example 4 by the method of Example 3.

Form: Dark yellow crystals
Yield: 70%
Melting point: 103.5–105° C.
$^1$H-NMR (80 MHz, CDCl$_3$) δ (ppm): 1.58–3.58 (m, 7H); 3.86 (s, 3H) 6.84–7.39 (m, 4H); 7.54–7.72 (d, 1H); 8.50 (d, 2H).
IR (cm$^{-1}$): 3020, 2940, 2840, 1675, 1600, 1590, 1580, 1470, 1260, 1045, 970, 740, 510

Production Example 13

Production of 6-methoxy-2-(4-pyridylmethyl)-1,2,3,4-tetrahydro-1-naphthalenone:

The title compound was produced from the compound of Production Example 7 by the method of Example 3.

Form: Colorless crystals
Yield: 83%
Melting point: 84–85° C.
$^1$H-NMR (400 MHz, CDCl$_3$) δ (ppm): 1.76–1.82, 2.03–2.09 (m, 2H) 2.66–2.77 (m, 2H); 3.44–3.48 (m, 1H); 3.85 (s, 3H); 6.67 (d, 1H); 6.83 (dd, 1H); 7.20 (d, 2H); 8.03 (d, 1H); 8.51 (d, 2H).
IR (cm$^{-1}$) 3060, 3010, 2940, 2840, 1670, 1605, 1495, 1255, 1135, 1030, 930, 845, 525

Production Example 14

Production of 7-methoxy-2-(4-pyridylmethyl)-1,2,3,4-tetrahydro-1-naphthalenone:

The title compound was produced from the compound of Production Example 5 by the method of Example 3.

Form: Colorless crystals
Yield: 79%
Melting point: 90–91.5° C.
$^1$H-NMR(80 MHz, CDCl$_3$) δ (ppm) 1.35–2.32 (m, 2H); 2.63–2.97 (m, 4H) 3.22–3.58 (m, 1H); 3.82 (s, 3H); 7.09–7.25 (m, 4H); 7.54–7.58 (m, 1H) 8.52 (d, 2H).
IR (cm$^{-1}$) 3060, 3010, 2980, 2920, 2820, 1670, 1605, 1490, 1415, 1245, 1030, 830, 510

Production Example 15

Production of 3-[(1-methyl-3,4-dihydro-2-naphthalenyl)methyl]pyridine:

The title compound was produced from the compound of Production Example 8 by the method of Example 4.
Form: Pale yellow oil substance
Yield: 64%
$^1$H-NMR (400 MHz, CDCl$_3$) δ (ppm): 2.16–2.17 (m, 2H); 2.68–2.72 (m, 2H); 3.63 (s, 2H); 7.11–7.33 (m, 5H); 7.51 (d, 1H); 8.45–8.51 (m, 2H)
IR (cm$^{-1}$) 3010, 2980, 2910, 2870, 2820, 1570, 1470, 1420, 1020, 760, 720

Production Example 16

Production of 3-[(5-methoxy-1-methyl-3,4-dihydro-2-naphthalenyl)methyl]pyridine:
The title compound was produced from the compound of Production Example 9 by the method of Example 4.
Form: Yellow oily substance
Yield: 63%
$^1$H-NMR (400 MHz, CDCl$_3$) δ (ppm): 2.11–2.17 (m, 5H); 2.68–2.72 (m, 2H); 3.63 (s, 2H); 3.82 (s, 3H); 6.78, 6.98 (d, 2H); 7.17–7.21 (m, 2H); 7.51 (d, 1H); 8.44–8.51 (m, 2H).
IR (cm$^{-1}$): 3010, 2980, 2920, 2820, 1570, 1465, 1435, 1260, 1045, 780, 710

Production Example 17

Production of 3-[(6-methoxy-1-methyl-3,4-dihydro-2-naphthalenyl)methyl]pyridine:
The title compound was produced from the compound of Production Example 10 by the method of Example 4.
Form: Orange oily substance
Yield: 48%
$^1$H-NMR (400 MHz, CDCl$_3$) δ (ppm): 2.14–2.16 (m, 5H); 2.66–2.69 (m, 2H); 3.61 (s, 2H) 3.80 (s, 3H); 6.68 (d, 1H); 6.75 (dd 1H); 7.18–7.26 (m, 2H); 7.51 (d, 1H); 8.44–8.50 (m, 2H).
IR (cm$^{-1}$) 3010, 2980, 2920, 2820, 1605, 1570, 1495, 1420, 1250, 1030, 710

Production Example 18

Production of 3-[(7-methoxy-1-methyl-3,4-dihydro-2-naphthalenyl)methyl]pyridine:
The title compound was produced from the compound of Production Example 11 by the method of Example 4.
Form: Brown oil substance
Yield: 65%
$^1$H-NHR (400 MHz, CDCl$_3$) δ (ppm): 2.13–2.15 (m, 5H); 2.61–2.65 (m, 2H); 3.63 (s, 2H); 3.82 (s, 3H); 6.68 (dd, 1H); 6.89 (d 1H); 7.01–7.03 (m, 1H); 7.18–7.21 (m, 1H); 7.51 (d, 1H); 8.46–8.50 (m, 2H).
IR (cm$^{-1}$): 3020, 2990, 2930, 2830, 1615, 1575, 1490, 1420, 1310, 1210, 1045, 720

Production Example 19

Production of 4-[(1-methyl-3,4-dihydro-2-naphthalenyl)methyl]pyridine:
The title compound was synthesized from a material compound, 2-(4-pyridylmethylene)-1,2,3,4-tetrahydro-1-naphthalenone and purified by crystallization with petroleum ether according to the method of Sam J. et al. (J. Pharm. Sci., 56, 644–47, 1967).
Form: Colorless crystals
Yield: 76%
Melting point: 67–69° C.
$^1$H-NHR (300 MHz, CDCl$_3$) δ (ppm): 2.13–2.18 (m, 5H); 2.68–2.79 (m, 2H); 3.63 (s, 2H); 7.06–7.24 (m, 5H); 7.33 (d 1H); 8.49 (d, 2H ).
IR (cm$^{-1}$): 3060, 3015, 2995, 2980, 2920, 2880, 2815, 1598, 1413, 995, 765, 473

Production Example 20

Production of 4-[(5-methoxy-1-methyl-3,4-dihydro-2-naphthalenyl)methyl]pyridine:
The title compound was produced from the compound of Production Example 12 by the method of Example 4.
Form: Colorless crystals
Yield: 52%
Melting point: 87–89° C.
$^1$H-NHR (80 MHz, CDCl$_3$) δ ((ppm): 1.62–2.32 (m, 5H); 2.48–2.93 (m, 2H); 3.60 (s, 2H); 3.79 (s, 3H); 6.62–7.34 (m, 4H); 7.49 (d, 1H); 8.45 (d, 2H).
IR (cm$^{-1}$): 3070, 2995, 2920, 2820, 1600, 1580, 1570, 1465, 1260, 1050, 795

Production Example 21

Production of 4-[(6-methoxy-1-methyl-3,4-dihydro-2-naphthalenyl)methyl]pyridine:
The title compound was produced from the compound of Production Example 13 by the method of Example 4.
Form: Pale green crystals
Yield: 64%
Melting point: 51–51.5° C.
$^1$H-NHR (80 MHz, CDCl$_3$) δ (ppm): 1.96–2.32 (m, 5H); 2.49–2.94 (m, 2H); 3.59 (s, 2H); 3.79 (s, 3H); 6.64–6.85 (m, 2H); 7.04–7.35 (m, 3H) 7.49 (d, 1H); 8.48 (d, 2H)
IR (cm$^{-1}$): 3020, 2930, 2840, 1610, 1505, 1420, 1255, 1040, 820

Production Example 22

Production of 4-[(7-methoxy-1-methyl-3,4-dihydro-2-naphthalenyl)methyl]pyridine:
The title compound was produced from the compound of Production Example 14 by the method of Example 4.
Form: Colorless crystals
Yield: 65%
Melting point: 57.5–58.5° C.
$^1$H-NHR (80 MHz, CDCl$_3$) δ (ppm): 1.92–2.29 (m, 5H); 2.43–2.84 (m, 2H); 3.60 (s, 2H); 3.79 (s, 3H); 6.63 (dd, 1H); 6.82–7.32 (m, 4H); 8.47 (d, 2H).
IR (cm$^{-1}$) 3000, 2920, 2820, 1610, 1590, 1485, 1420, 1200, 1035, 810, 510

Production Example 23

Production of 5-methyl-6-(3-pyridylmethyl)-7,8-dihydro-1-naphthalenol:
The title compound was produced from the compound of Production Example 16 by the method of Example 5.
Form: White solid
Yield: 71%
Melting point: 171–173° C.
$^1$H-NHR (400 MHz, d$_6$-DMSO) δ (ppm): 2.05–2.09 (m, 2H); 2.51–2.59 (m, 2H); 3.75 (s, 2H); 6.70, 6.80 (d, 2H); 6.98–7.02 (m, 1H); 7.71 (dd 1H); 8.07 (d, 1H); 8.64–8.67 (m, 2H); 9.20 (s, 1H).
IR (cm$^{-1}$) 3020 (large),2900, 2740, 2700, 1570, 1550, 1460, 1300, 1285, 1165, 940, 785

Production Example 24

Production of 5-methyl-6-(3-pyridylmethyl)-7,8-dihydro-2-naphthalenol:
The title compound was produced from the compound of Production Example 17 by the method of Example 5.
Form: White crystals
Yield: 57%
Melting point: 180–182° C.
$^1$H-NMR (400 MHz, d$_6$-DMSO) δ (ppm): 2.03–2.09 (m, 5H); 2.50–2.55 (m, 2H); 3.59 (s, 2H); 6.52 (d, 1H); 6.58 (dd, 1H); 7.10 (d, 1H); 7.25–7.29 (m, 1H); 8.07 (d, 1H); 8.40–8.45 (m, 2H); 9.25 (s, 1H)
IR (cm$^{-1}$) 2980 (br),2900, 2820, 2680, 2600, 1610, 1600, 1595, 1425, 1290, 1255, 1160, 815, 710

Production Example 25

Production of 8-methyl-7-(3-pyridylmethyl)-5,6-dihydro-2-naphthalenol:

The title compound was produced from the compound of Production Example 18 by the method of Example 5.
Form: Brown solid
Yield: 53%
Melting point: 145–147.5° C.
$^1$H-NMR (400 MHz, $d_6$-DMSO) δ (ppm): 1.96–2.13 (m, 5H); 2.45–2.56 (m, 2H); 3.62 (s, 2H); 6.51–6.52 (m, 1H); 6.72–6.73 (m, 1H); 6.87–6.89 (m, 1H); 7.25–7.31 (m, 1H); 7.70–7.72 (m, 1H); 8.41–8.46 (m, 2H); 9.08 (s, 1H).
IR (cm$^{-1}$) 3000 (br),2900, 2810, 2650, 1610, 1570, 1475, 1420, 1300, 1040, 805, 710

Production Example 26

Production of 5-methyl-6-(4-pyridylmethyl)-7,8-dihydro-1-naphthalenol:

The title compound was produced from the compound of Production Example 20 by the method of Example 4.
Form: White solid
Yield: 43%
Melting point: 158–160.5° C.
$^1$H-NMR (400 MHz, $d_6$-DMSO) δ (ppm): 2.03–2.09 (m, 5H); 2.50–2.58 (m, 2H); 3.62 (s, 2H); 6.68–6.70, 6.78–6.80, 7.00–7.01 (m, 3H); 7.23 (d, 2H); 8.45 (d, 2H); 9.18 (s, 1H).
IR (cm$^{-1}$): 3040 (br),2910, 2820, 2650, 1600, 1570, 1460, 1300, 1280, 1000, 785

Production Example 27

Production of 5-methyl-6-(4-pyridylmethyl)-7,8-dihydro-2-naphthalenol:

The title compound was produced from the compound of Production Example 21 by the method of Example 4.
Form: White solid
Yield: 88%
Melting point: 197.5–200° C.
$^1$H-NMR (400 MHz, $d_6$-DMSO) δ (ppm): 2.03–2.09 (m, 5H); 2.47–2.55 (m, 2H); 3.59 (s, 2H); 6.53–6.60 (m, 2H); 7.09–7.23 (m, 3H); 8.45 (d, 2H) 9.18 (s, 1H).
IR (cm$^{-1}$) 2980 (br),2910, 2870, 2810, 2670, 2650, 1600, 1450, 1255, 1005, 810, 780

Production Example 28

Production of 8-methyl-7-(4-pyridylmethyl)-5,6-dihydro-2-naphthalenol:

The title compound was produced from the compound of Production Example 22 by the method of Example 4.
Form: Brown solid
Yield: 93%
Melting point: 146.5–147° C.
$^1$H-NMR (400 MHz, $d_6$-DMSO) δ (ppm): 1.99–2.08 (m, 5H); 2.50–2.54 (m, 2H); 3.62 (s, 2H); 6.51–6.54, 6.72–6.73, 6.88–6.90 (m, 3H); 7.23 (d, 2H); 8.46 (d, 2H); 9.10 (s, 1H).
IR (cm$^{-1}$) 3000 (br),2900, 2810, 2640, 1600, 1570, 1420, 1340, 1305, 1190, 1005, 810, 620

Production Example 29

Production of 5-methoxy-2-[1-(4-pyridyl)methylidene]-1,2,3,4-tetrahydro-1-naphthalenone:

The title compound was produced from 5-methoxy-1-tetralone and pyridine-4-carbaldehyde by the method of Example 6.
Form: Brown crystals
Yield: 60%
Melting point: 144–145° C.
$^1$H-NMR (80 MHz, CDCl$_3$) δ (ppm): 2.78–3.20 (m, 4H); 3.86 (s, 3H) 6.97–7.47 (m, 4H); 7.58–7.86 (m, 2H); 8.62 (dd, 2H).
IR (cm$^{-1}$): 3000, 2950, 2820, 2660, 1600, 1590, 1475, 1265, 1025, 970, 750, 535

Production Example 30

Production of 7-methoxy-2-[1-(4-pyridyl)methylidene]-1,2,3,4-tetrahydro-1-naphthalenone:

The title compound was produced from 7-methoxy-1-tetralone and pyridine-4-carbaldehyde by the method of Example 6.
Form: Pale yellow crystals
Yield: 84%
Melting point: 134.5–135° C.
$^1$H-NMR (400 MHz, CDCl$_3$) δ (ppm): 2.90–3.06 (m, 2H); 3.07–3.09 (m, 2H); 3.88 (s, 3H); 7.09–7.11 (m, 1H); 7.18–7.20 (m, 1H); 7.28 (2H) 7.61 (d, 1H); 7.72 (s, 1H); 8.67 (dd, 2H).
IR (cm$^{-1}$): 3060, 3020, 2960, 2900, 2830, 1660, 1590, 1490, 1320, 1255, 1030, 830, 750, 530

Production Example 31

Production of 6-methoxy-2-[1-(4-pyridyl)methylidene]-1,2,3,4-tetrahydro-1-naphthalenone:

The title compound was produced from 6-methoxy-1-tetralone and pyridine-4-carbaldehyde by the method of Example 7.
Form: Pale yellow crystals
Yield: 78%
Melting point: 127.5–128.5° C.
$^1$H-NMR (400 MHz, CDCl$_3$) δ ((ppm): 2.93–2.96 (m, 2H); 3.05–3.09 (m, 2H); 3.88 (s, 3H); 6.71 (d, 1H); 6.89 (dd, 1H); 7.27 (d, 2H); 7.70 (s, 1H, —CH═); 8.12 (d, 1H); 8.66 (d, 2H).
IR (cm$^{-1}$) 3020, 2970, 2840, 1665, 1600, 1590, 1490, 1325, 1275, 1140, 950

Production Example 32

Production of 2-[1-(1H-4-imidazolyl)methylidene]-6-methoxy-1,2,3,4-tetrahydro-1-naphthalenone:

The title compound was produced from 6-methoxy-1-tetralone and 1H-imidazolyl-4-carbaldehyde by the method of Example 6.
Form: Pale yellow crystals
Yield: 84%
Melting point: 154–155° C. 融点: 154~155° C.
$^1$H-NMR (80 MHz, $d_6$-DMSO) δ (ppm): 2.86 (t, 2H); 3.37 (t, 2H); 3.83 (s, 3H); 6.79–7.05 (m, 2H); 7.58 (s, 2H); 7.85–8.05 (m, 2H).
IR (cm$^{-1}$): 3100, 2900, 2820, 2590, 1660, 1610, 1585, 1440, 1330, 1305, 1255, 1130, 1095, 830, 620, 590

Production Example 33

Production of 5-methoxy-2-(4-pyridylmethyl)-1,2,3,4-tetrahydro-1-naphthalenone:

The title compound was produced from the compound of Production Example 29 by the method of Example 8.
Form: Dark yellow amorphous powder
Yield: 70%
Melting point: 103.5–105° C.
$^1$H-NMR (80 MHz, CDCl$_3$) δ (ppm): 1.58–3.58 (m, 7H); 3.86 (s, 3H); 6.84–7.39 (m, 4H); 7.54–7.72 (d, 1H); 8.50 (d, 2H).
IR (cm$^{-1}$): 3020, 2940, 2840, 1675, 1600, 1590, 1580, 1470, 1260, 1045, 970, 740, 510

Production Example 34

Production of 6-methoxy-2-(4-pyridylmethyl)-1,2,3,4-tetrahydro-1-naphthalenone:

The title compound was produced from the compound of Production Example 31 by the method of Example 8.

Form: Colorless crystals
Yield: 83%
Melting point: 84–85° C.
$^1$H-NMR (400 MHz, CDCl$_3$) δ (ppm): 1.76–1.82, 2.03–2.09 (m, 2H); 2.66–2.77 (m, 2H); 3.44–3.48 (m, 1H); 3.85 (s, 3H); 6.67 (d, 1H); 6.83 (dd, 1H); 7.20 (d, 2H); 8.03 (d, 1H); 8.51 (d, 2H).
IR (cm$^{-1}$) 3060, 3010, 2940, 2840, 1670, 1605, 1495, 1255, 1135, 1030, 930, 845, 525

Production Example 35
Production of 7-methoxy-2-(4-pyridylmethyl)-1,2,3,4-tetrahydro-1-naphthalenone:
The title compound was produced from the compound of Production Example 30 by the method of Example 8.
Form: Colorless crystals
Yield: 79%
Melting point: 90–91.5° C.
$^1$H-NMR (80 MHz, CDCl$_3$) δ (ppm): 1.35–2.32 (m, 2H); 2.63–2.97 (m, 4H); 3.22–3.58 (m, 1H); 3.82 (s, 3H); 7.09–7.25 (m, 4H); 7.54–7.58 (m, 1H), 8.52 (d, 2H).
IR (cm$^{-1}$) 3060, 3010, 2980, 2920, 2820, 1670, 1605, 1490, 1415, 1245, 1030, 830, 510

Production Example 36
Production of 2-(1H-imidazolylmethy)-6-methoxy-1,2,3,4-tetrahydro-1-naphthalenone:
The title compound was produced from the compound of Production Example 32 by the method of Example 8.
Form: Colorless crystals
Yield: 70%
Melting point: 148–150° C.
$^1$H-NMR (80 MHz, d$_6$-DMSO) δ (ppm): 1.46–3.30 (m, 7H); 3.81 (s, 3H) 6.67–7.24 (m, 3H); 7.50 (s, 1H); 7.91 (d, 1H).
IR (cm$^{-1}$) 3100, 2920, 2840, 2820, 2560, 1655, 1595, 1350, 1250, 1100, 1020, 930, 825, 660, 580, 440

Production Example 37
Production of 4-[(1-ethyl-5-methoxy-3,4-dihydro-2-naphthalenyl)methyl]pyridine:
The title compound was produced from the compound of Production Example 33 by the method of Example 9.
Form: Yellow solid
Yield: 5%
Melting point: 59–62° C.
$^1$H-NMR (400 MHz, CDCl$_3$) δ (ppm): 1.13 (t, 3H); 2.08 (t, 2H); 2.56–2.68 (m, 4H) 3.63 (s, 2H); 3.82 (s, 3H); 6.79 (d, 1H); 7.02 (d, 1H) 7.16–7.24 (m, 3H); 8.50 (s, 2H).
IR (cm$^{-1}$) 3060, 2980, 2930, 2830, 1600, 1570, 1470, 1410, 1310, 1260, 1160, 1060, 1050, 990, 940, 790, 730

Production Example 38
Production of 4-[(1-ethyl-6-methoxy-3,4-dihydro-2-naphthalenyl)methyl]pyridine, hydrochloride:
The title compound was produced from the compound of Production Example 34 by the method of Example 9.
Form: Colorless crystals
Yield: 41%
Melting point: 134–137° C.
$^1$H-NMR (400 MHz, d$_6$-DMSO) δ (ppm): 1.02 (t, 3H); 2.08 (t, 2H); 2.57 (q, 2H); 2.65 (t, 2H); 3.74 (s, 3H); 3.91 (s, 2H); 6.72–6.81 (m, 2H); 7.27 (d, 1H); 7.89 (d, 2H); 8.81 (d, 2H).
IR (cm$^{-1}$): 3060, 3020, 2960, 2935, 2880, 2835, 1610, 1570, 1415, 1255, 1160, 1125, 1080, 1040, 990, 820, 620

Production Example 39
Production of 4-[(1-ethyl-7-methoxy-3,4-dihydro-2-naphthalenyl)methyl]pyridine:
The title compound was produced from the compound of Production Example 35 by the method of Example 9.
Form: Pale yellow oily substance
Yield: 13%
$^1$H-NMR (400 MHz, CDCl$_3$) δ (ppm): 1.15 (t, 3H); 2.10 (t, 2H) 2.56–2.68 (m, 4H); 3.63 (s, 2H); 3.82 (s, 3H); 6.68 (d, 1H); 6.93 (s, 1H) 7.04 (d, 2H); 7.89 (s, 2H); 8.50 (s, 2H).
IR (cm$^{-1}$) 3030, 3010, 2960, 2930, 2880, 2830, 1600, 1570, 1490, 1410, 1310, 1275, 1215, 1045, 870, 800

Production Example 40
Production of 4-[(6-methoxy-1-methyl-3,4-dihydro-2-naphthalenyl)methyl]-1-1H-imidazole:
The title compound was produced from the compound of Production Example 36 by the method of Example 9.
Form: White solid
Yield: 29%
Melting point: 171–173° C.
$^1$H-NMR (400 MHz, d$_6$-DMSO) δ (ppm): 2.02 (s, 3H); 2.15 (t, 2H); 2.61 (t, 2H); 3.44 (s, 2H); 3.72 (s, 3H); 6.65–6.79 (m, 3H); 7.16 (d, 1H); 7.51 (s, 1H)
IR (cm$^{-1}$): 3100, 3060, 2960, 2920, 2880, 1605, 1500, 1460, 1310, 1255, 1170, 1030, 830

Production Example 41
Production of 4-[(5-methoxy-3,4-dihydro-2-naphthalenyl)methyl]pyridine:
The title compound was produced from the compound of Production Example 33 by the method of Example 9.
Form: Pale yellow solid
Yield: 8%
Melting point: 75–77° C.
$^1$H-NMR (400 MHz, CDCl$_3$) δ (ppm): 2.16 (t, 2H); 2.79 (t, 2H); 3.49 (s, 2H); 3.81 (s, 3H); 6.24 (s, 1H); 6.66–6.73 (each d, each 1H); 7.11 (t, 1H); 7.18 (d, 2H); 8.52 (s, 2H).
IR (cm$^{-1}$): 3060, 3000, 2960, 2920, 2880, 2830, 1600, 1590, 1470, 1440, 1270, 1095, 995, 895, 725

Production Example 42
Production of 4-[(6-methoxy-3,4-dihydro-2-naphthalenyl)methyl]pyridine:
The title compound was produced from the compound of Production Example 34 by the method of Example 11.
Form: Orange crystals
Yield: 77%
Melting point: 63–64° C.
$^1$H-NMR (400 MHz, CDCl$_3$) δ (ppm): 2.15 (t, 2H); 2.77 (t, 2H); 3.47 (s, 2H); 3.79 (s, 3H); 6.23 (s, 1H); 6.58 (d, 1H); 6.66 (dd, 1H); 6.99 (d, 1H); 7.18 (d, 2H); 8.51 (d, 2H).
IR (cm$^{-1}$) 3060, 3040, 3000, 2980, 2940, 2920, 2830, 1615, 1600, 1570, 1400, 1250, 1150, 1110, 1060, 800, 790, 590, 475

Production Example 43
Production of 4-[(7-methoxy-3,4-dihydro-2-naphthalenyl)methyl]pyridine:
The title compound was produced from the compound of Production Example 35 by the method of Example 8.
Form: Pale yellow oily substance
Yield: 11%
$^1$H-NMR (400 MHz, CDCl$_3$) δ (ppm): 2.16 (t, 2H); 2.72 (t, 2H); 3.49 (s, 2H); 3.78 (s, 3H); 6.23 (s, 1H); 6.58 (d, 1H); 6.66 (dd, 1H); 6.99 (d, 1H); 7.18 (d, 2H); 8.51 (d, 2H).
IR (cm$^{-1}$): 3060, 3020, 3000, 2930, 2830, 1605, 1580, 1500, 1420, 1270, 1220, 1140, 1040, 815

Production Example 44

Production of 4-[(6-methoxy-1-propyl-3,4-dihydro-2-naphthalenyl)methyl]pyridine, hydrochloride:

The title compound was produced from the compound of Production Example 34 by the method of Example 9.

Form: Colorless crystals
Yield: 19%
Melting point: 145–147° C.
$^1$H-NMR (400 MHz, $d_6$-DMSO) δ (ppm): 0.91 (t, 3H); 1.36–1.45 (m, 2H) 2.07 (t, 2H); 2.53 (t, 2H); 2.65 (t, 2H); 3.74 (s, 3H); 3.92 (s, 2H); 6.74–6.80 (m, 2H); 7.25 (d, 1H); 7.89 (d, 2H); 8.81 (d, 2H).
IR ($cm^{-1}$): 3040, 2940, 2870, 2830, 2460, 2105, 2005, 1635, 1615, 1605, 1500, 1310, 1255, 1035, 1005, 850, 820, 790

Production Example 45

Production of 6-(4-pyridylmethyl)-7,8-dihydro-2-naphthalenol:

The title compound was produced from the compound of Production Example 42 by the method of Example 10.

Form: Yellow amorphous powder
Yield: 8%
Melting point: >300° C.
$^1$H-NMR (400 MHz, $CDCl_3$) δ ((ppm): 2.05 (t, 2H); 2.61 (t, 2H); 3.46 (s, 2H); 6.21 (s, 1H); 6.44–6.55 (m, 2H); 6.82 (d, 1H); 7.26 (d, 2H); 8.47 (d, 2H); 9.25 (s, 1H).
IR ($cm^{-1}$) 3120 (large),3020, 2920, 1610, 1500, 1420, 1285, 1150, 1010, 820, 790

Production Example 46

Production of 2-(1H-4-imidazolylmethyl)-6-methoxy-3,4-dihydronaphthalene, hydrochloride:

The title compound was produced from the compound of Production Example 36 by the method of Example 11.

Form: Colorless crystals
Yield: 58%
Melting point: 184–186° C.
$^1$H-NMR (400 MHz, $d_6$-DMSO) δ ((ppm): 2.17 (t, 2H); 2.73 (t, 2H); 3.56 (s, 2H); 3.72 (s, 3H); 6.22 (s, 1H); 6.63–6.74 (m, 2H); 6.95 (d, 1H); 7.50 (s, 1H); 9.06 (s, 1H); 14.58 (s, 1H).
IR ($cm^{-1}$) 3080, 3000, 2820, 2600, 1620, 1580, 1500, 1260, 1160, 1115, 1040, 860, 810, 635

Production Example 47

Production of 2-[1-(1H-4-imidazolyl)methylidene]-7-methoxy-1,2,3,4-tetrahydro-1-naphthalenone:

The title compound was produced from 7-methoxy-1-tetralone and imidazolyl-4-carbaldehyde by the method of Example 12.

Form: Pale yellow crystals
Yield: 94%
Melting point: 162–164° C.
$^1$H-NMR (80 MHz, $d_6$-DMSO) δ (ppm): 2.72–3.04 (m, 2H); 3.20–3.58 (m, 2H); 3.80 (s, 3H); 7.02–7.51 (m, 3H); 7.47–7.68 (m, 2H); 7.83 (s, 1H) 11.8 (s, 1H);
IR ($cm^{-1}$) 3110, 3015, 2925, 2845, 2180, 2120, 1670, 1600, 1400, 1030, 830, 620

Production Example 48

Production of 2-(1H-4-imidazolylmethy)-7-methoxy-1,2,3,4-tetrahydro-1-naphthalenone:

The title compound was produced from the compound of Production Example 47 by the method of Example 13.

Form: Colorless crystals
Yield: 44%
Melting point: 158–160° C.
$^1$H-NMR (80 MHz, $d_6$-DMSO) δ (ppm): 1.73–2.41 (m, 3H); 2.57–3.15 (m, 4H); 3.82 (s, 3H); 6.83 (s, 1H); 6.95–7.22 (m, 2H); 7.24–7.55 (m, 2H);
IR ($cm^{-1}$): 3110, 2990, 2950, 2930, 2840, 1680, 1615, 1500, 1300, 1040, 635

Production Example 49

Production of 4-[7-methoxy-1-methyl-3,4-dihydro-2-naphthalenyl)methyl]-1H-imidazole:

The title compound was produced from the compound of Production Example 48 by the method of Example 14.

Form: Brown solid
Yield: 15%
Melting point: 133–135° C.
$^1$H-NMR (400 MHz, $d_6$-DMSO) δ (ppm): 2.09 (s, 3H); 2.22 (t, 2H); 2.64 (t, 2H); 3.59 (s, 2H); 3.81 (s, 3H); 6.67 (dd, 1H); 6.79 (s, 1H); 6.86 (d, 1H); 7.01 (d, 1H); 7.57 (s, 1H);
IR ($cm^{-1}$): 3070, 3000, 2930, 2830, 2620, 1610, 1570, 1490, 1275, 1205, 1045, 990, 870, 840, 815, 735, 630

Production Example 50

Production of 2-[1-(1H-4-imidazolyl)methylidene]-5-methoxy-1,2,3,4-tetrahydro-1-naphthalenone:

The title compound was produced using 5-methoxy-1-tetralone by the method of Example 15.

Form: Yellow crystals
Yield: 87%
Melting point: 194.0–195.0° C.
$^1$H-NMR (500 MHz, DMSO-$d_6$) δ (ppm): 2.86 (t, 2H, J=6.5 Hz); 3.36 (t, 2H, J=6.5 Hz); 3.83 (s, 3H); 7.18 (d, 1H, J=7.9 Hz); 7.32 (t, 1H, J=7.9 Hz); 7.55 (d, 1H, J=7.9 Hz); 7.55 (s, 1H); 7.62 (s, 1H); 7.85 (s, 1H).
IR (KBr; $cm^{-1}$): 3450, 3100, 2850, 1660, 1580, 1310, 1260, 1140, 1080, 1020
FAB-MS: 255 (M+1)
Element Analysis: $C_{15}H_{14}N_2O_2 \cdot \frac{1}{2}H_2O$=263.30 Calculated: C; 68.43, H; 5.74, N; 10.64 Found: C; 68.80, H; 5.59, N; 10.89

Production Example 51

Production of 2-(1H-4-imidazolylmethyl)-5-methoxy-1,2,3,4-tetrahydro-1-naphthalenone:

The title compound was produced from the compound of Production Example 50 by the method of Example 16.

Form: Colorless crystals
Yield: 83%
Melting point: 145.5–148.0° C.
$^1$H-NHR (500 MHz, $CDCl_3$) δ (ppm): 1.59 (m, 1H) 2.04 (ddd, 1H, J=4.3, 8.9, 13.5 Hz); 2.51 (dd, 1H, J=9.1, 15.0 Hz); 2.56 (m, 1H): 2.73 (m, 1H); 2.90 (dt, 1H, J=4.3, 17.7 Hz); 3.08 (dd, 1H, J=4.0, 14.6 Hz); 6.78 (s, 1H); 7.11 (dd, 1H, J=0.9, 7.9 Hz); 7.23 (t, 1H, J=7.9 Hz); 7.42 (dd, 1H, J=0.9, 7.9 Hz); 7.57 (d, 1H, J=0.9 Hz).
IR (KBr; $cm^{-1}$): 3450, 3050, 2820, 1680, 1580, 1460, 1250, 1100, 1040, 940
FAB-MS: 257 (M+1)
Element Analysis: $C_{15}H_{16}N_2O_2$=256.30 Calculated: C; 70.29, H; 6.29, N; 10.93 Found: C; 69.97, H; 5.83, N; 10.98

Production Example 52

Production of 4-[(5-methoxy-1-methyl-3,4-dihydro-2-naphthalenyl)methyl]-1H-imidazole:

The title compound was produced from the compound of Production Example 51 using methyl magnesium iodide by the method of Example 17.

Form: White crystalline powder
Yield: 66%
Melting point: 132.5–135.0° C.
$^1$H-NHR (500 MHz, $d_6$-DMSO) δ (ppm): 2.03 (s, 3H) 2.13 (t, 2H, J=8.5 Hz): 2.58 (t, 2H, J=8.5 Hz); 3.45 (s, 2H); 3.74 (s, 3H); 6.73 (s, 1H); 6.82 (d, 1H, J=8.2 Hz);6.89 (d, 1H, J=8.2 Hz); 7.13 (t, 1H, J=8.2 Hz); 7.50 (s, 1H); 11.76 (br s, 1H)

IR (KBr cm$^{-1}$):3400, 3100, 2830, 1680, 1590, 1570, 1510, 1480, 1400, 1260

FAB-MS: 255 (M+1)

Element Analysis: $C_{16}H_{18}N_2O \cdot \frac{1}{2}H_2O = 263.34$ Calculated: C; 72.98, H; 7.27, N; 10.64 Found: C; 73.19, H; 7.01, N; 11.11

Production Example 53

Production of 4-[(1-ethyl-6-methoxy-3,4-dihydro-2-naphthalenyl)methyl]-1H-imidazole:

The title compound was produced from the compound of Production Example 36 using ethyl magnesium bromide by the method of Example 17.

Form: Brown crystalline powder
Yield: 32%
Melting point: 138.0–141.5° C.
$^1$H-NHR (500 MHz, $d_6$-DMSO) δ (ppm): 1.02 (t, 3H, J=7.3 Hz); 2.12 (t, 2H, J=7.6 Hz); 2.52 (dd, 2H, J=7.3, 15.0 Hz); 2.58 (t, 2H, J=7.6 Hz); 3.42 (s, 2H); 3.71 (s, 3H); 6.69–6.89 (m, 3H); 7.17 (d, 1H, J=6.6 Hz); 7.48 (s, 1H); 11.75 (br s, 1H).
IR (KBr; cm$^{-1}$):3450, 3050, 2830, 1600, 1500, 1460, 1300, 1250, 1170, 1040
FAB-MS: 269 (M+1)
Element Analysis: $C_{17}H_{20}N_2O = 268.36$ Calculated: C; 76.09, H; 7.51, N; 10.44 Found: C; 76.11, H; 7.26, N; 10.30

Production Example 54

Production of 4-[(1-ethyl-7-methoxy-3,4-dihydro-2-naphthalenyl)methyl]-1H-imidazole:

The title compound was produced from the compound of Production Example 48 using ethyl magnesium bromide by the method of Example 17.

Form: White crystalline powder
Yield: 33%
Melting point: 111.5–113.5° C.
$^1$H-NHR (500 MHz, $d_6$-DMSO) δ (ppm): 1.04 (t, 3H, J=7.6 Hz); 2.13 (t, 2H, J=7.6 Hz); 2.51–2.57 (m, 4H); 3.45 (s, 2H); 3.72 (s, 3H) 6.70 (dd, 1H, J=2.5, 8.2 Hz); 6.74 (br s, 1H); 6.79 (d, 1H, J=2.5 Hz); 7.00 (d, 1H, J=8.2 Hz); 7.49 (s, 1H); 11.76 (br s, 1H).
IR (KBr; cm$^{-1}$): 3450, 3060, 2830, 1600, 1570, 1490, 1270, 1170, 1040, 980
FAB-MS: 269 (M+1)
Element Analysis: $C_{17}H_{20}N_2O = 268.36$ Calculated: C; 76.09, H; 7.51, N; 10.44 Found: C; 75.74, H; 7.01, N; 10.86

Production Example 55

Production of 4-[(1-ethyl-5-methoxy-3,4-dihydro-2-naphthalenyl)methyl]-1H-imidazole hydrochloride:

The title compound was produced from the compound of Production Example 51 using ethyl magnesium bromide by the method of Example 17.

Form: Brown crystals
Yield: 14%
Melting point: 164.0–166.0° C.
$^1$H-NHR (500 MHz, $d_6$-DMSO) δ (ppm): 1.00 (t, 3H, J=7.6 Hz); 2.10 (t, 2H, J=8.0 Hz); 2.55 (dd, 2H, J=7.5, 15.1 Hz); 2.61 (t, 2H, J=7.6 Hz); 3.65 (s, 2H); 3.76 (s, 3H); 6.85 (d, 1H, J=7.6 Hz); 6.96 (d, 1H, J=7.9 Hz); 7.17 (dd, 1H, J=7.6, 7.9 Hz); 7.38 (d, 1H, J=1.2 Hz); 9.02 (d, 1H, J=1.2 Hz); 14.59 (br s, 2H).
IR (KBr; cm$^{-1}$): 3390, 3080, 2950, 2820, 1610, 1570, 1460, 1250, 1040, 770
FAB-MS: 269 (M+1)
Element Analysis: $C_{17}H_{20}N_2O \cdot HCl = 304.82$ Calculated: C; 66.99, H; 6.94, N; 9.19 Found: C; 66.76, H; 6.64, N; 9.43

Production Example 56

Production of 4-[(6-methoxy-1-propyl-3,4-dihydro-2-naphthalenyl)methyl]-1H-imidazole:

The title compound was produced from the compound of Production Example 36 using propyl magnesium bromide by the method of Example 17.

Form: Colorless crystals
Yield: 12%
Melting point: 123.5–124.5° C.
$^1$H-NHR (500 MHz, $d_6$-DMSO) δ (ppm): 0.90 (t, 3H, J=6.4 Hz); 1.41 (m, 2H); 2.11 (dd, 2H, J=7.6, 7.9 Hz); 2.49 (m, 2H); 2.58 (dd, 2H, J=7.6, 8.0 Hz); 3.44 (s, 2H); 3.71 (s, 3H); 6.69–6.72 (m, 3H) 7.16 (d, 1H, J=8.5 Hz); 7.48 (s, 1H); 11.72 (br s, 1H).
IR (KBr cm$^{-1}$) 3430, 3070, 2950, 1600, 1490, 1460, 1300, 1240, 1030, 930, 820
Element Analysis: $C_{18}H_{22}N_2O = 282.39$ Calculated: C; 76.55, H; 7.85, N; 9.92 Found: C; 76.43, H; 8.04, N; 10.20

Production Example 57

Production of 4-[(5-methoxy-1-propyl-3,4-dihydro-2-naphthalenyl)methyl]-1H-imidazole:

The title compound was produced from the compound of Production Example 51 using propyl magnesium bromide by the method of Example 17.

Form: White crystalline powder
Yield: 47%
Melting point: 174.5–175.5° C.
$^1$H-NHR (500 MHz, $d_6$-DMSO) δ (ppm): 0.91 (t, 3H, J=7.5 Hz); 1.54 (m, 1H); 1.78 (m, 1H); 2.02 (dt, 1H, J=7.3, 14.9 Hz); 2.17 (dt, 1H, J=7.3, 14.9 Hz); 2.36 (m, 1H); 2.44–6.67 (m, 3H); 3.19 (br s, 1H); 3.28 (br s, 1H); 3.76 (s, 3H); 5.92 (t, 1H, J=7.32); 6.78 (d, 1H, J=7.94); 7.08–7.15 (m, 2H); 7.49 (s, 1H); 11.73 (br s, 1H).
IR (KBr; cm$^{-1}$): 3430, 3050, 2900, 1560, 1460, 1430, 1250, 1100, 980, 820, 770 FAB-MS: 283 (M+1)
Element Analysis: $C_{18}H_{22}N_2O = 282.39$ Calculated: C; 76.55, H; 7.85, N; 9.92 Found: C; 76.05, H; 7.73, N; 9.84

Production Example 58

Production of 4-[(6-methoxy-1-phenyl-3,4-dihydro-2-naphthalenyl)methyl]-1H-imidazole:

The title compound was produced from the compound of Production Example 36 by the method of Example 18.

Form: Colorless crystals
Yield: 31%
Melting point: 201.5–202.5° C.
$^1$H-NHR (500 MHz, $d_6$-DMSO) δ ((ppm) 2.25 (dd, 2H, J=7.6, 8.2 Hz); 2.76 (dd, 2H, J=7.6, 8.2 Hz); 3.22 (s, 2H); 3.69 (s, 3H); 6.38 (d, 1H, J=8.5 Hz); 6.57 (dd, 1H, J=2.7, 8.5 Hz); 6.73 (br s, 1H); 6.75 (d, 1H, J=2.7 Hz); 7.23 (d, 2H, J=7.0 Hz); 7.32 (t, 1H, J=7.3 Hz); 7.40 (dd, 1H, J=7.3, 7.6 Hz); 7.37 (s, 1H); 11.73 (br s, 1H).
IR (KBr; cm$^{-1}$) 3450, 3050, 2850, 1600, 1570, 1490, 1240, 1100, 1030, 810, 700
FAB-MS: 317 (M+1)
Element Analysis: $C_{21}H_{20}N_2O = 316.40$ Calculated: C; 79.72, H; 6.37, N; 8.85 Found: C; 79.25, H; 6.46, N; 8.94

Production Example 59

Production of 4-[(7-methoxy-1-phenyl-3,4-dihydro-2-naphthalenyl)methyl]-1H-imidazole:

The title compound was produced from the compound of Production Example 48 by the method of Example 18.

Form: Colorless crystals
Yield: 42%
Melting point: 198.5–199.5° C.
$^1$H-NHR (500 MHz, $d_6$-DMSO) δ (ppm): 2.25 (dd, 2H, J=7.6, 8.2 Hz); 2.71 (dd, 2H, J=7.6, 8.2 Hz); 3.22 (s, 2H);

3.53 (s, 3H) 5.99 (d, 1H, J=2.7 Hz); 6.66 (dd, 1H, J=2.7, 8.2 Hz); 6.73 (s, 1H) 7.07 (d, 1H, J=8.2 Hz); 7.25 (d, 2H, J=8.2 Hz); 7.34 (dd, 1H, J=7.3, 7.6 Hz); 7.40 (dd, 2H, J=7.0, 7.6 Hz); 7.48 (d, 1H, J=0.9 Hz); 11.75 (br s, 1H).

IR (KBr cm$^{-1}$): 3430, 3050, 2920, 1600, 1480, 1460, 1300, 1200, 1040, 980, 700

FAB-MS: 317 (M+1)

Element Analysis: $C_{21}H_{20}N_2O$=316.40 Calculated: C; 79.72, H; 6.37, N; 8.85 Found: C; 79.58, H; 6.40, N; 8.99

Production Example 60

Production of 4-[(5-methoxy-1-phenyl-3,4-dihydro-2-naphthalenyl)methyl]-1H-imidazole:

The title compound was produced from the compound of Production Example 51 by the method of Example 18.

Form: Colorless crystals
Yield: 39%
Melting point: 200.0–202.0° C.
$^1$H-NHR (500 MHz, d$_6$-DMSO) δ (ppm): 2.23 (dd, 2H, J=7.9, 8.5 Hz); 2.73 (dd, 2H, J=7.9, 8.5 Hz); 3.20 (s, 2H); 3.77 (s, 3H); 6.10 (d, 1H, J=8.0 Hz); 6.73 (s, 1H); 6.80 (d, 1H, J=8.2 Hz); 6.97 (d, 1H, J=8.0 Hz); 7.23 (d, 2H, J=7.3 Hz); 7.32 (dd, 1H, J=7.0, 7.6 Hz); 7.40 (dd, 2H, J=7.3, 7.9 Hz); 7.48 (s, 1H); 11.74 (br s, 1H).

IR (KBr cm$^{-1}$): 3450, 3050, 2850, 1580, 1460, 1250, 1210, 1070, 980, 940, 700

FAB-MS: 317 (M+1)

Element Analysis: $C_{21}H_{20}N_2O$=316.40 Calculated: C; 79.72, H; 6.37, N; 8.85 Found: C; 79.41, H; 6.40, N; 8.87

Production Example 61

Production of 4-[(1-benzyl-6-methoxy-3,4-dihydro-2-naphthalenyl)methyl]-1H-imidazole:

The title compound was produced from the compound of Production Example 36 by the method of Example 19.

Form: Colorless crystals
Yield: 29%
Melting point: 122.5–123.0° C.
$^1$H-NHR (500 MHz, d$_6$-DMSO) δ (ppm): 2.28 (dd, 2H, J=7.6, 8.2 Hz); 2.76 (dd, 2H, J=7.3, 8.2 Hz); 3.67 (s, 2H); 3.93 (s, 3H); 6.58 (dd, 1H, J=2.7, 8.5 Hz); 6.68 (d, 1H, J=2.4 Hz); 6.74 (s, 1H); 7.01 (d, 1H, J=8.5 Hz); 7.11 (m, 1H); 7.21 (m, 4H); 7.51 (s, 1H); 11.83 (br s, 1H).

IR (KBr; cm$^{-1}$):3430, 2930, 2830, 1610, 1570, 1490, 1300, 1280, 1250, 1040

FAB-MS: 331 (M+1)

Element Analysis: $C_{21}H_{20}N_2O$=330.43 Calculated: C; 79.97, H; 6.71, N; 8.48 Found: C; 79.65, H; 6.65, N; 8.24

Production Example 62

Production of 4-[(5-methoxy-3,4-dihydro-2-naphthalenyl)methyl]-1H-imidazole, Hydrochloride:

The title compound was produced from the compound of Production Example 51 by the method of Example 17.

Form: Colorless crystals
Yield: 19%
Melting point: 192.5–194.5° C.
$^1$H-NHR (500 MHz, d$_6$-DMSO) δ (ppm): 2.17 (dd, 2H, J=8.2, 8.5 Hz); 2.70 (dd, 2H, J=8.2, 8.5 Hz); 3.57 (s, 2H); 3.75 (s, 3H); 6.22 (s, 1H) 6.64 (d, 1H, J=7.3 Hz); 6.81 (d, 1H, J=8.2 Hz); 7.09 (t, 1H, J=7.9 Hz); 7.49 (s, 1H); 9.04 (s, 1H); 14.54 (br s, 2H).

IR (KBr cm$^{-1}$): 3450, 3080, 2800, 1610, 1570, 1460, 1260, 1080, 840, 620

FAB-MS: 241 (M+1)

Element Analysis: $C_{15}H_{16}N_2O \cdot HCl$=276.77 Calculated: C; 65.10, H; 6.19, N; 10.12 Found: C; 65.51, H; 6.17, N; 10.16

Production Example 63

Production of 4-[(7-methoxy-3,4-dihydro-2-naphthalenyl)methyl]-1H-imidazole:

The title compound was produced from the compound of Production Example 48 by the method of Example 17.

Form: Colorless crystals
Yield: 5%
Melting point: 155.5–156.5° C.
$^1$H-NHR (500 MHz, d$_6$-DMSO) δ (ppm): 2.16 (dd, 2H, J=8.0, 8.3 Hz); 2.70 (dd, 2H, J=8.0, 8.3 Hz); 3.38 (s, 2H); 3.68 (s, 3H); 6.18 (s, 1H) 6.56 (d, 1H, J=2.4 Hz); 6.61 (dd, 1H, J=2.4, 8.2 Hz); 6.79 (s, 1H) 6.97 (d, 1H, J=8.2 Hz); 7.51 (s, 1H); 11.80 (br s, 1H)

IR (KBr; cm$^{-1}$): 3450, 3070, 3000, 1600, 1500, 1460, 1300, 1260, 1210, 1030

FAB-MS: 241 (M+1)

Element Analysis: $C_{15}H_{16}N_2O$=240.31 Calculated: C; 74.97, H; 6.71, N; 11.66 Found: C; 74.97, H; 6.67, N; 11.45

Production Example 64

Production of 5-ethoxy-2-[1-(1H-4-imidazolyl)methylidene]-1,2,3,4-tetrahydro-1-naphthalenone:

The title compound was produced using 5-ethoxy-1-tetralone by the method of Example 15.

Form: Brown crystals
Yield: 82%
Melting point: 122.0–124.0° C.
$^1$H-NMR (500 MHz, DMSO-d$_6$) δ (ppm) 1.37 (dd, 3H, J=6.7, 7.0 Hz); 2.86 (dd, 2H, J=6.4, 6.7 Hz); 3.42 (dd, 2H, J=6.4, 6.7 Hz); 4.07 (dd, 2H, J=7.0, 13.7 Hz); 7.18 (d, 1H, J=7.9 Hz); 7.31 (t, 1H, J=7.9 Hz); 7.52 (s, 1H); 7.53 (d, 1H, J=7.9 Hz); 7.64 (s, 1H); 7.82 (s, 1H); 12.44 (br s, 1H)

IR (KBr; cm$^{-1}$): 3450, 3100, 2970, 1660, 1570, 1460, 1320, 1260, 1060, 1020

FAB-MS: 269 (M+1)

Element Analysis: $C_{16}H_{16}N_2O_2$=268.32 Calculated: C; 71.62, H; 6.01, N; 10.44. Found: C; 71.41, H; 6.06, N; 10.19.

Production Example 65

Production of 5-ethoxy-2-(1H-4-imidazolylmethyl)-1,2,3,4-tetrahydro-1-naphthalenone:

The title compound was produced from the compound of Production Example 64 by the method of Example 16.

Form: Brown crystalline powder
Yield: 80%
Melting point: 132.0–134.0° C.
$^1$H-NHR (500 MHz, CDCl$_3$) δ (ppm): 1.34 (dd, 3H, J=6.7, 7.0 Hz); 1.65 (m, 1H); 2.10 (m, 1H); 2.54 (dd, 1H, J=8.9, 14.7 Hz); 2.63 (m, 1H); 2.78 (m, 1H); 2.97 (dt, 1H, J=4.3, 17.7 Hz); 3.11 (dd, 1H, J=4.3, 14.7 Hz); 4.06 (m, 2H); 6.79 (s, 1H); 7.17 (d, 1H, J=7.9 Hz); 7.28 (t, 1H, J=7.9 Hz); 7.46 (d, 1H, J=7.9 Hz); 7.57 (d, 1H, J=0.9 Hz) IR (KBr; cm$^{-1}$) 3430, 3050, 2950, 1680, 1580, 1460, 1250, 1100, 1040, 940

FAB-MS: 271 (M+1)

Element Analysis: $C_{16}H_{18}N_2O_2$=270.33 Calculated: C; 71.09, H; 6.71, N; 10.36 Found: C; 70.62, H; 6.66, N; 10.22

Production Example 66

Production of 6-ethoxy-2-[1-(1H-4-imidazolyl)methylidene]-1,2,3,4-tetrahydro-1-naphthalenone:

The title compound was produced using 6-ethoxy-1-tetralone by the method of Example 15.

Form: Brown crystalline powder
Yield: 62%
Melting point: 133.5–134.5° C.
$^1$H-NMR (500 MHz, CDCl$_3$) δ (ppm): 1.32 (dd, 3H, J=6.7, 7.0 Hz); 2.95 (dd, 2H, J=6.4, 6.7 Hz); 3.34 (br s, 2H); 4.08 (q, 2H, J=7.0 Hz); 6.69 (d, 1H, J=2.4 Hz); 6.83 (dd, 1H, J=2.4, 8.5 Hz); 7.38 (s, 1H) 7.76 (s, 2H); 8.04 (d, 1H, J=8.6 Hz).

IR (KBr; cm$^{-1}$): 3450, 3100, 2900, 1610, 1330, 1270, 1130, 1040, 1000, 760

FAB-MS: 269 (M+1)
Element Analysis: $C_{16}H_{16}N_2O_2$=268.32 Calculated: C; 71.62, H; 6.01, N; 10.44 Found: C; 71.71, H; 6.09, N; 10.36

Production Example 67

Production of 6-ethoxy-2-(1H-4-imidazolylmethyl)-1,2,3,4-tetrahydro-1-naphthalenone:

The title compound was produced from the compound of Production Example 66 by the method of Example 16.
Form: Brown crystalline powder
Yield: 92%
Melting point: 143.5–144.5C
$^1$H-NMR (500 MHz, DMSO-$d_6$) δ (ppm): 1.32 (dd, 3H, J=6.7, 7.0 Hz); 1.66 (m, 1H); 2.04 (m, 1H); 2.53 (dd, 1H, J=9.1, 14.7 Hz); 2.72 (m, 1H); 2.88 (dd, 2H, J=4.9, 5.2 Hz); 3.12 (dd, 1H, J=4.0, 14.6 Hz); 4.09 (dd, 2H, J=7.0, 13.7 Hz); 6.76 (s, 1H); 6.80 (d, 1H, J=2.4 Hz); 6.86 (dd, 1H, J=2.4, 8.5 Hz); 7.49 (s, 1H); 7.83 (d, 1H, J=8.8 Hz); 11.77 (br s, 1H).
IR (KBr; cm$^{-1}$):3430, 3100, 2970, 1660, 1600, 1470, 1350, 1270, 1210, 1100
FAB-MS: 271 (M+1)
Element Analysis: $C_{16}H_{18}N_2O_2$=270.33 Calculated: C; 71.09, H; 6.71, N; 10.36 Found: C; 71.52, H; 6.72, N; 10.27

Production Example 68

Production of 7-ethoxy-2-[1-(1H-4-imidazolyl)methylidene]-1,2,3,4-tetrahydro-1-naphthalenone:

The title compound was produced using 7-ethoxy-1-tetralone by the method of Example 15.
Form: Brown crystals
Yield: 55%
Melting point: 139.5–141.0° C.
$^1$H-NMR (500 MHz, DMSO-$d_6$) δ (ppm): 1.33 (t, 3H, J=7.0 Hz); 2.86 (dd, 2H, J=6.4, 6.7 Hz); 3.35 (br s, 2H); 4.05 (q, 2H, J=7.0 Hz); 7.10 (dd, 1H, J=2.7, 8.2 Hz); 7.27 (d, 1H, J=8.5 Hz); 7.39 (d, 1H, J=2.7 Hz); 7.56 (s, 1H); 7.63 (s, 1H); 7.85 (s, 1H); 12.54 (br s, 1H).
IR (KBr; cm$^{-1}$):3450, 3150, 2900, 1650, 1570, 1490, 1420, 1320, 1240, 1120
FAB-MS: 269 (M+1)
Element Analysis: $C_{16}H_{16}N_2O_2$=268.32 Calculated: C; 71.62, H; 6.01, N;10.44 Found: C; 71.33, H; 6.40, N; 10.36

Production Example 69

Production of 7-ethoxy-2-(1H-4-imidazolylmethyl)-1,2,3,4-tetrahydro-1-naphthalenone:

The title compound was produced from the compound of Production Example 68 by the method of Example 16.
Form: Colorless crystals
Yield: 59%
Melting point: 176.5–178.5° C.
$^1$H-NMR (500 MHz, DMSO-$d_6$) δ (ppm): 1.31 (dd, 3H, J=6.7, 7.0 Hz); 1.66 (m, 1H); 2.06 (m, 1H); 2.56 (dd, 1H, J=9.1, 14.6 Hz); 2.77 (m, 1H); 2.85 (m, 1H); 3.13 (dd, 1H, J=3.9, 14.6 Hz); 4.03 (dd, 2H, J=6.7, 13.7 Hz); 6.78 (s, 1H); 7.10 (dd, 1H, J=2.7, 8.5 Hz); 7.22 (d, 1H, J=2.7 Hz); 7.51 (s, 1H); 11.79 (br s, 1H).
IR (KBr; cm$^{-1}$): 3450, 3130, 2950, 1660, 1610, 1500, 1270, 1240, 1050, 920
FAB-MS: 271 (M+1)
Element Analysis: $C_{16}H_{18}N_2O_2$=270.33 Calculated: C; 71.09, H; 6.71, N; 10.36 Found: C; 71.01, H; 7.10, N; 10.37

Production Example 70

Production of 4-[(5-ethoxy-1-methyl-3,4-dihydro-2-naphthalenyl)methyl]-1H-imidazole:

The title compound was produced from the compound of Production Example 65 using methyl magnesium iodide by the method of Example 17.
Form: Colorless crystals
Yield: 56%
Melting point: 133.5–136.0° C.
$^1$H-NHR (500 MHz, $d_6$-DMSO) δ (ppm): 1.31 (t, 3H, J=7.0 Hz); 2.03 (s, 3H); 2.13 (dd, 2H, J=7.3, 7.9 Hz); 2.59 (dd, 2H, J=7.9, 8.2 Hz); 3.45 (s, 2H); 4.00 (dd, 2H, J=7.0, 13.7 Hz); 6.72 (s, 1H); 6.80 (d, 1H, J=8.2 Hz); 6.88 (d, 1H, J=7.6 Hz); 7.11 (t, 1H, J=8.0 Hz); 7.49 (s, 1H); 11.76 (br s, 1H).
IR (KBr, cm$^{-1}$): 3450, 3070, 2980, 1580, 1460, 1400, 1260, 1060, 990, 820
FAB-MS: 269 (M+1)
Element analysis: $C_{17}H_{20}N_2O_2$=268.36 Calculated: C; 76.09, H; 7.51, N; 10.44 Found: C; 75.62, H; 7.78, N; 10.82

Production Example 71

Production of 4-[(6-ethoxy-1-methyl-3,4-dihydro-2-naphthalenyl)methyl]-1H-imidazole:

The title compound was produced from the compound of Production Example 67 using methyl magnesium iodide by the method of Example 17.
Form: Colorless crystals
Yield: 47%
Melting point: 126.0–127.0° C.
$^1$H-NHR (500 MHz, $d_6$-DMSO) δ (ppm): 1.29 (t, 3H, J=7.0 Hz); 2.01 (s, 3H); 2.14 (t, 2H, J=7.3 Hz); 2.59 (dd, 2H, J=7.6, 7.9 Hz); 3.43 (s, 2H); 3.97 (q, 2H, J=7.0 Hz); 6.66 (d, 1H, J=2.7 Hz); 6.70 (dd, 1H, J=2.7, 8.5 Hz); 6.71 (s, 1H); 7.13 (d, 1H, J=8.5 Hz); 7.49 (d, 1H, J=0.9 Hz); 11.76 (br s, 1H).
IR (KBr, cm$^{-1}$):3450, 3000, 2830, 1610, 1570, 1500, 1480, 1250, 1160, 1120
FAB-MS: 269 (M+1)
Element analysis: $C_{17}H_{20}N_2O_2$=304.82 Calculated: C; 76.09, H; 7.51, N; 10.44 Found: C; 75.86, H; 7.22, N; 10.39

Production Example 72

Production of 4-[(7-ethoxy-1-methyl-3,4-dihydro-2-naphthalenyl)methyl]-1H-imidazole Hydrochloride:

The title compound was produced from the compound of Production Example 69 using methyl magnesium iodide by the method of Example 17.
Form: Colorless crystals
Yield: 12%
Melting point: 170.5–171.5° C.
$^1$H-NHR (500 MHz, $d_6$-DMSO) δ (ppm): 1.30 (dd, 3H, J=6.7, 7.0 Hz); 2.05 (s, 3H); 2.13 (dd, 2H, J=7.0, 7.6 Hz); 2.58 (dd, 2H, J=7.6, 7.9 Hz); 3.65 (s, 2H); 3.99 (dd, 2H, J=7.0, 13.7 Hz); 6.68 (dd, 1H, J=2.4, 7.9 Hz); 6.80 (d, 1H, J=2.4 Hz); 7.01 (d, 1H, J=8.2 Hz); 7.40 (s, 1H); 9.02 (s, 1H); 14.56 (br s, 2H).
IR (KBr, cm$^{-1}$):3400, 3120, 2970, 1610, 1510, 1480, 1440, 1320, 1250, 1050
FAB-MS: 269 (M+1)
Element analysis: $C_{17}H_{20}N_2O_2$.HCl;304.82 Calculated: C; 66.99, H; 6.94, N; 9.19 Found: C; 66.49, H; 7.23, N; 9.38

Production Example 73

Production of 2-[1-(1H-4-imidazolyl)methylidene)-6-propoxy-1,2,3,4-tetrahydro-1-naphthalenone:

The title compound was produced using 6-propoxy-1-tetralone by the method of Example 15.
Form: Brown crystals
Yield: 38%
Melting point: 156.5–158.0° C.
$^1$H-NMR (500 MHz, DMSO-$d_6$) δ (ppm): 0.96 (dd, 3H, J=7.0, 7.3 Hz); 1.73 (dd, 2H, J=6.7, 13.7 Hz); 2.90 (t, 2H, J=6.1 Hz); 3.35 (br s, 2H); 4.00 (t, 2H, J=6.4 Hz); 6.86 (s, 1H); 6.89 (d, 1H, J=8.8 Hz); 7.52 (s, 1H) 7.58 (s, 1H); 7.81 (s, 1H); 7.87 (d, 1H, J=8.6 Hz).

IR (KBr; cm$^{-1}$):3430, 3130, 2950, 1660, 1600, 1280, 1260, 1120, 1100, 1020

FAB-MS: 283 (M+1)

Element Analysis: $C_{17}H_{18}N_2O_2$=282.34 Calculated: C; 72.32, H; 6.43, N; 9.92 Found: C; 72.16, H; 6.50, N; 9.85

Production Example 74

Production of 2-(1H-4-imidazolylmethyl)-6-propoxy-1,2,3,4-tetrahydro-1-naphthalenone:

The title compound was produced from the compound of Production Example 73 by the method of Example 16.

Form: Colorless crystals

Yield: 87%

Melting point: 134.5–136.0° C.

$^1$H-NMR (500 MHz, DMSO-d$_6$) δ (ppm): 0.96 (dd, 3H, J=7.3, 7.6 Hz); 1.66–1.74 (m, 3H); 2.03 (m, 1H); 2.53 (m, 1H); 2.72 (m, 1H); 2.89 (br s, 1H); 3.12 (d, 1H, J=11.3 Hz); 3.99 (t, 2H, J=6.4 Hz); 6.76 (s, 1H); 6.82 (s, 1H); 6.87 (d, 1H, J=7.0 Hz); 7.50 (s, 1H); 7.82 (d, 1H, J=8.6 Hz); 11.74 (br s, 1H).

IR (KBr; cm$^{-1}$):3450, 2950, 1670, 1610, 1480, 1360, 1280, 1220, 1110, 1020

FAB-MS: 285 (M+1)

Element Analysis: $C_{17}H_{20}N_2O_2$=284.36 Calculated: C; 71.81, H; 7.09, N; 9.85 Found: C; 71.55, H; 7.20, N; 9.71

Production Example 75

Production of 4-[(1-methyl-6-propoxy-3,4-dihydro-2-naphthalenyl)methyl]-1H-imidazole:

The title compound was produced from the compound of Production Example 74 using methyl magnesium iodide by the method of Example 17.

Form: Colorless crystals

Yield: 31%

Melting point: 91.5–92.0° C.

$^1$H-NMR (500 MHz, DMSO-d$_6$) δ (ppm): 0.95 (dd, 3H, J=7.3, 7.6 Hz); 1.69 (m, 2H); 2.01 (s, 3H); 2.14 (t, 2H, J=7.6 Hz); 3.35 (dd, 2H, J=7.6, 7.9 Hz); 3.42 (s, 2H); 3.88 (t, 2H, J=6.4 Hz); 6.68–6.71 (m, 3H); 7.13 (d, 1H, J=8.5 Hz); 7.48 (s, 1H); 11.71 (br s, 1H).

IR (KBr; cm$^{-1}$): 3500, 2950, 1600, 1560, 1490, 1460, 1240, 1010, 980, 790

FAB-MS: 283 (M+1)

Element analysis: $C_{18}H_{22}N_2O$=282.39 Calculated: C; 76.56, H; 7.85, N; 9.92 Found: C; 76.56, H; 7.71, N; 9.94

Production Example 76

Production of 2-[1-(1H-4-imidazolyl)methylidene)-6-isobutoxy-1,2,3,4-tetrahydro-1-naphthalenone:

The title compound was produced using 6-isobutoxy-1-tetralone by the method of Example 15.

Form: Yellow crystals

Yield: 63%

Melting point: 79.0–81.5° C.

$^1$H-NMR (500 MHz, DMSO-d$_6$) δ (ppm): 0.98 (d, 6H, J=6.7 Hz); 2.03 (m, 1H); 2.90 (t, 2H, J=6.7 Hz); 3.25–3.40 (br m, 2H); 3.83 (d, 2H, J=6.4 Hz); 6.88 (d, 1H, J=2.1 Hz); 6.91 (dd, 1H, J=2.4, 8.5 Hz); 7.51 (br s, 1H); 7.58 (br s, 1H); 7.81 (s, 1H); 7.87 (d, 1H, J=8.55 Hz); 12.4 (br s, 1H).

IR (KBr; cm$^{-1}$): 3420, 1660, 1600, 1580, 1330, 1270, 1130, 1100, 1030, 990

FAB-MS: 297 (M+1)

Element Analysis: $C_{18}H_{20}N_2O_2$=296.37 Calculated: C; 72.95, H; 6.80, N; 9.45 Found: C; 72.64, H; 7.05, N; 9.16

Production Example 77

Production of 2-(1H-4-imidazolylmethyl)-6-isobutoxy-1,2,3,4-tetrahydro-1-naphthalenone:

The title compound was produced from the compound of Production Example 76 by the method of Example 16.

Form: Colorless crystals

Yield: 66%

Melting point: 114.5–115.0° C.

$^1$H-NMR (500 MHz, DMSO-d$_6$) δ (ppm):0.96 (d, 6H, J=6.7 Hz); 1.67 (m, 1H) 2.02 (m, 1H); 2.05 (m, 1H); 2.63 (m, 1H); 2.72 (m, 1H); 2.88 (m, 2H); 3.12 (dt, 1H, J=3.1, 14.3 Hz); 3.81 (d, 2H, J=6.4 Hz); 6.62–6.88 (m, 3H); 7.49 (d, 1H, J=14.3 Hz); 7.82 (d, 1H, J=8.9 Hz); 11.74 (d, 1H, J=17.7 Hz).

IR (KBr; cm$^{-1}$): 3450, 1670, 1590, 1470, 1240, 1100, 1010, 940, 820, 660

FAB-MS: 299 (M+1)

Element Analysis: $C_{18}H_{22}N_2O_2$=298.39 Calculated: C; 72.46, H; 7.43, N; 9.39 Found: C; 72.40, H; 7.16, N; 9.44

Production Example 78

Production of 4-[(6-isobutoxy-1-methyl-3,4-dihydro-2-naphthalenyl)methyl]-1H-imidazole:

The title compound was produced from the compound of Production Example 77 using methyl magnesium iodide by the method of Example 17.

Form: Colorless crystals

Yield: 67%

Melting point: 96.0–97.0° C.

$^1$H-NMR (500 MHz, DMSO-d$_6$) δ (ppm):0.95 (d, 6H, J=6.7 Hz); 1.97 (m, 4H) 2.09 (m, 1H); 2.16 (dd, 1H, J=6.7, 7.3 Hz); 2.57 (dd, 2H, J=6.7, 7.3 Hz); 3.39 (br s, 1H); 3.47 (br s, 1H); 3.70 (d, 2H, J=6.4 Hz); 6.60–6.71 (m, 3H) 7.13 (dd, 1H, J=8.4, 15.4 Hz); 7.47 (d, 1H, J=10.1 Hz); 11.72 (br s, 1H).

IR (KBr; cm$^{-1}$): 3430, 1620, 1490, 1470, 1250, 1070, 1030, 990, 860, 830, 800

FAB-MS: 298 (M+1)

Element analysis: $C_{19}H_{24}N_2O$=294.41 Calculated: C; 76.99, H; 8.16, N; 9.45 Found: C; 76.95, H; 8.06, N; 9.58

Test Example 1

17α-Hydroxylase/$C_{17-20}$-lyase Inhibiting Activity:

The experiment was carried out as follows according to the method of T. Sergejew and R. W. Hartmann (J. Enzyme Inhibition, 8, 113, 1994): Testes from SD male rats or surgically removed human testes were homogenized and then centrifuged to obtain microsomes. A test compound was introduced into a microtube (1.5 ml, Eppendolf), then 100 μl of microsome protein, in which the protein concentration was adjusted to 0.1 mg/ml with a 50 mM phosphate buffer solution (pH 7.4), 140 μl of a 125 nmol NADPH solution, and 10 μL of 6.25 nmol progesterone was added, and the admixture was incubated at 37° C. for 20 minutes. To this were added 50 μl of 1 N hydrochloric acid, then 1 ml of ethyl acetate, and the admixture was mixed, then centrifuged. The resulting ethyl acetate layer was washed with 250 μl of a 50 mM phosphate buffer solution (pH 7.4) and 50 μl of 1 N hydrochloric acid. After centrifugation and concentration, the resulting concentrate was dissolved in 100 μl of acetonitrile. A portion of this solution (10 μl) was subjected to high performance liquid chromatography. The amounts of substrates and products, i.e., 17α-hydroxyprogesterone, androstenedione, and testosterone, were measured to calculate enzyme activities. In the control groups, no test compound was added. 17α-Hydroxylase/$C_{17-20}$-lyase inhibiting activity (%) was calculated from the amounts of corresponding substrate and product using the following calculation formula. Results are shown in Table 1 and Table 2.

Calculation Formula 1:

Inhibiting activity (%)=100−(Enzyme activity with inhibitor/Enzyme activity with no inhibitor)×100

TABLE 1

17α-Hydroxylase/C$_{17-20}$-lyase inhibiting activity

| Production | Inhibiting activity (%) | | IC$_{50}$ (μM) | | Relative activity | |
|---|---|---|---|---|---|---|
| Example | Rat | Human | Rat | Human | Rat | Human |
| 15 | 84 | 42 | 14.3 | —*¹ | 5 | — |
| 16 | 86 | 79 | 12 | 0.63 | 6 | 1 |
| 17 | 93 | 84 | 3.6 | 0.51 | 19 | 1 |
| 18 | 77 | 42 | 13 | — | — | — |
| 23 | 82 | 36 | 16 | — | 4 | — |
| 24 | 86 | 79 | 2.6 | 0.51 | 26 | 1 |
| 25 | 98 | 88 | 1.8 | 0.28 | 37 | 3 |
| 19 | 99 | 91 | 1.8 | — | 37 | — |
| 20 | 99 | 98 | 0.57 | — | 130 | — |
| 21 | 99 | 94 | 1.1 | 0.15 | 60 | 5 |
| 22 | 99 | 96 | 0.62 | 0.064 | 110 | 11 |
| 26 | 95 | 95 | 0.38 | 0.12 | 180 | 6 |
| 27 | 100 | 99 | 0.11 | 0.036 | 610 | 20 |
| 28 | 100 | 99 | 0.27 | 0.058 | 250 | 13 |
| 37 | — | 98 | — | 0.072 | — | 10 |
| 38 | 98 | 95 | 0.50 | 0.12 | 130 | 6 |
| 39 | — | 96 | — | 0.12 | — | 6 |
| 40 | 100 | 98 | 0.28 | 0.11 | 240 | 7 |
| 41 | — | 98 | — | 0.083 | — | 9 |
| 42 | 98 | 92 | 1.1 | 0.22 | 60 | 3 |
| 43 | 98 | 89 | — | 0.31 | — | 2 |
| 44 | 100 | 88 | 2.1 | 0.28 | 30 | 3 |
| 45 | 100 | 95 | 1.7 | 0.16 | 40 | 3 |
| 46 | 100 | 90 | 1.3 | 0.13 | 50 | 6 |
| 49 | — | 96 | 13 | — | — | — |

*¹Not determined.

Enzyme source: Rat testis microsomes
Inhibitor concentration: 125 μM (inhibiting activity (%) was calculated)
Substrate concentration: 25 μM (progesterone)
NADPH concentration: 250 μM
Relative activity: Ketoconazole=1 (IC$_{50}$=67 μM)
Enzyme source: Human testis microsomes
Inhibitor concentration: 2.5 μM (inhibiting activity (%) was calculated)
Substrate concentration: 25 μM (progesterone)
NADPH concentration: 300 μM
Relative activity: Ketoconazole=1 (IC$_{50}$=0.74 μM)

TABLE 2

17α-Hydroxylase/C$_{17-20}$-lyase inhibiting activity

| Production Example | Inhibiting activity (%) | Production Example | Inhibiting activity (%) |
|---|---|---|---|
| 50 | 12 | 65 | 13 |
| 51 | 11 | 66 | 8 |
| 52 | 13 | 67 | 11 |
| 53 | 43 | 68 | 10 |
| 54 | 17 | 69 | 5 |
| 55 | 10 | 70 | 18 |
| 56 | 18 | 71 | 31 |
| 57 | 12 | 72 | 28 |
| 58 | 11 | 73 | 14 |
| 59 | 15 | 74 | 15 |
| 60 | 12 | 75 | 10 |
| 61 | 8 | 76 | 13 |
| 62 | 12 | 77 | 13 |
| 63 | 9 | 78 | 12 |
| 64 | 13 | | |

Enzyme source: Rat testis microsomes
Inhibitor concentration: 50 μM
Substrate concentration: 25 μM(progesterone)
NADPH concentration: 250 μM Test Example 2
Thromboxan A$_2$ Synthesis Inhibiting Activity Test:
Measurement was done as follows according to the method of Rolf W. Hartmann et al. (Arch. Pharm. Pharm. Med. Chem., 329, 251, 1996). To 0.5 ml of citric acid-treated human whole blood were added 10 μl of an ethanol/K-Na-phosphate buffer solution (pH 7.4) containing a test compound, and the admixture was preincubated at 37° C. for 10 minutes. Dazoxybene hydrochloride (100 μM) was added to the blanks. Next, 50 μl of a collagen solution (final collagen concentration: 53.6 μg/ml) were added and incubation was continued at 37° C. for 10 minutes. The reaction was stopped by adding 0.4 ml of a 20% trichloroacetic acid solution in 0.6 M hydrochloric acid, and the admixture was centrifuged at 4400× g for 10 minutes. The resulting supernatant (0.5 ml) was fractionated and added to 0.5 ml of a 0.53% thiobarbituric acid solution (solvent: K-Na-phosphate buffer (pH 7.4)), and the admixture was heated for 70 minutes and then allowed to stand at room temperature for 30 minutes. This sample was measured by a fluorophotometer (excitation wave length: 533 nm, measurement wave length: 550 nm). Control samples without test compounds were tested in the same manner. The inhibiting activity (%) was calculated from the measurements using formula 1. Results are shown in Table 3.

TABLE 3

Thromboxane A$_2$ synthesis inhibiting activity

| Production Example | Inhibiting activity (%) |
|---|---|
| 19 | 25 |
| 20 | 60 |
| 21 | 43 |

Enzyme source: Citric acid-treated human whole blood
Inhibitor concentration: 50 μM (inhibiting activity (%) was calculated)
Substrate concentration: 25 μM (progesterone)

Test Example 3
Aromatase Inhibiting Activity Test:
Measurement was done according to the method of Rolf W. Hartmann and Christine Batzl (J. Med. Chem., 29, 8, 1368, 1986).
(1) Preparation of Aromatase:
Aromatase was prepared from the microsome fraction of human placenta tissue according to the method of Thompson and Siiteri (J. Biol. Chem., 249, 5346, 1974). Microsomes obtained were suspended in a phosphate buffer solution (0.05 M, pH 7.4) and stored at −30° C. The stored enzyme showed no change in its activity for 4 months.

(2) Aromatase Inhibiting Activity:

Enzyme activity was evaluated by measuring the amount of $^3H_2O$ produced by [1β, 2β-$^3$H] testosterone during the reaction according to the methods of Foster A. B. et al. (Foster A. B. et al., J. Med. Chem., 26, 50, 1983) and Graves P. E. and Salhanick H. A. (Endocrinology, 105, 52, 1979) as follows. To a test tube containing 0.225 μCi of [1β, 2β-$^3$H] testosterone were added 5 μM unlabeled testosterone, 2 mM NADPH, 20 mM glucose-6-phosphate, 1EU of glucose-6-phosphate dehydrogenase, and a test compound (0–250 μM) dissolved in phosphate buffer (0.05 M, pH 7.4). The test compound was dissolved in ethanol and diluted with the phosphate buffer. The final ethanol concentration in a reaction solution of the control and the test compound was 2%. This test tube was preincubated in a water bath at 30° C. for 5 minutes. Next, 0.5 mg of the microsome enzyme was added to start the reaction. The total volume of the reaction solution was 0.5 ml. Water phase portions (100 μl) were taken 0, 7, 14, and 21 minutes after the start of the reaction and added to 200 μl of cold 1 mM $HgCl_2$. To this were added 200 μl of a 2% dextran-treated activatd charcoal (DCC) suspension. The admixture was shaken for 20 minutes and then centrifuged at 1500× g for 5 minutes to isolate the steroid adsorbed on DCC. The amount of the produced $^3H_2O$ in the fractionated supernatant was counted by a liquid scintillation counter. Control samples with no test compound were tested in the same manner. The inhibiting activity (%) was calculated from the measurement using calculation formula 1. Results are shown in Table 4.

TABLE 4

Aromatase inhibiting activity

| Production Example | Inhibiting activity (%) | $IC_{50}$ [μM] |
|---|---|---|
| 15 | 56 | —[*1] |
| 16 | 50 | — |
| 17 | 52 | — |
| 18 | 61 | — |
| 23 | 60 | — |
| 24 | 37 | — |
| 25 | — | 6.4 |
| 19 | — | 0.23 |
| 20 | — | 0.38 |
| 21 | — | 0.65 |
| 22 | — | 0.63 |
| 26 | — | 0.70 |
| 27 | — | 1.3 |
| 28 | — | 1.2 |
| 37 | — | 0.95 |
| 38 | — | 0.79 |
| 39 | — | 1.3 |
| 40 | — | 1.2 |
| 41 | — | 0.95 |
| 42 | — | 0.79 |
| 43 | — | 1.7 |
| 44 | — | 0.86 |

TABLE 4-continued

Aromatase inhibiting activity

| Production Example | Inhibiting activity (%) | $IC_{50}$ [μM] |
|---|---|---|
| 45 | — | 3.5 |
| 46 | — | 1.8 |

[*1]Not determined.

Enzyme source: Human placenta microsomes
Inhibitor concentration: 25 μM (inhibiting activity (%) was calculated)
Substrate concentration: 2.5 μM (testosterone)
NADPH concentration: 250 μM

What is claimed is:

1. Dihydronaphthalene compound of formula (I) or a pharmaceutically acceptable acid or base salt thereof,

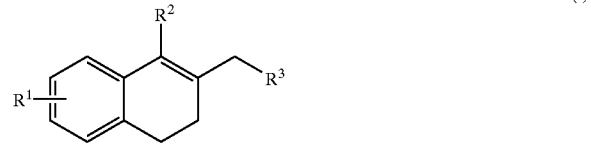

(I)

wherein $R^1$ represents hydrogen, hydroxyl methoxyl, ethoxyl, propoxyl, or isobutoxyl; $R^2$ represents hydrogen, methyl, ethyl, propyl, phenyl, or benzyl; and $R^3$ represents 3-pyridyl, 4-pyridyl, or 4-1H-imidazolyl, provided that when $R^3$ is 4-pyridyl, $R^1$ is hydroxyl, and when $R^3$ is 3-pyridyl $R^2$ is phenyl or benzyl.

2. The dihydronaphthalene compound or a pharmaceutically acceptable acid or base salt thereof according to claim 1 wherein $R^1$ is methoxyl, ethoxyl, propoxyl, or isobutoxyl, and $R^3$ is 4-1H-imidazolyl.

3. The dihydronaphthalene compound or a pharmaceutically acceptable acid or base salt thereof according to claim 1, wherein $R^1$ is methoxyl, $R^2$ is hydrogen or methyl, and $R^3$ is 4-1H-imidazolyl.

4. The dihydronaphthalene compound or a pharmaceutically acceptable acid or base salt thereof according to claim 1, wherein $R^1$ is hydroxyl, $R^2$ is hydrogen or methyl, and $R^3$ is 4-pyridyl.

5. 5-methyl-6-(4-pyridylmethyl)-7,8-dihydro-2-naphthalenol.

6. 8-methyl-7-(4-pyridylmethyl)-5,6-dihydro-2-naphthalenol.

7. A pharmaceutical composition comprising a dihydronaphthalene compound or a pharmaceutically acceptable acid or base salt thereof according to any one of claims 1 to 3 or 4–6 in an amount effective to exhibit an activity selected from the group consisting of 17α-hydroxylase inhibiting activity and $C_{17-20}$-lyase inhibiting activity, and a pharmaceutically acceptable carrier.

* * * * *